US008524754B2

(12) United States Patent
Zamansky et al.

(10) Patent No.: US 8,524,754 B2
(45) Date of Patent: Sep. 3, 2013

(54) POLYMORPHIC, CRYSTALLINE AND MESOPHASE FORMS OF SODIUM 2-(5-BROMO-4-(4-CYCLOPROPYLNAPH-THALEN-1-YL)-4H-1,2,4-TRIAZOL-3-YLTHIO) ACETATE, AND USES THEREOF

(75) Inventors: Irina Zamansky, Oceanside, CA (US); Jean-Luc Girardet, San Diego, CA (US); Gabriel Galvin, San Diego, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 13 days.

(21) Appl. No.: 13/375,607

(22) PCT Filed: Jan. 5, 2011

(86) PCT No.: PCT/US2011/020233
§ 371 (c)(1),
(2), (4) Date: Feb. 9, 2012

(87) PCT Pub. No.: WO2011/085009
PCT Pub. Date: Jul. 14, 2011

(65) Prior Publication Data
US 2012/0129903 A1 May 24, 2012

Related U.S. Application Data

(60) Provisional application No. 61/293,602, filed on Jan. 8, 2010.

(51) Int. Cl.
*A61K 31/41* (2006.01)
*A61K 31/44* (2006.01)
*A61K 31/56* (2006.01)
*C07D 249/00* (2006.01)

(52) U.S. Cl.
USPC ...... 514/383; 514/384; 548/262.2; 548/263.8

(58) Field of Classification Search
USPC .................... 514/383, 384; 548/262.2, 263.8
See application file for complete search history.

(56) References Cited

U.S. PATENT DOCUMENTS

| 7,435,752 | B2 | 10/2008 | Girardet et al. | |
|---|---|---|---|---|
| 8,003,681 | B2 | 8/2011 | Girardet et al. | |
| 8,084,483 | B2 | 12/2011 | Quart et al. | |
| 8,283,369 | B2 | 10/2012 | Quart et al. | |
| 8,357,713 | B2 | 1/2013 | Quart et al. | |
| 2006/0270725 | A1 | 11/2006 | Girardet et al. | |
| 2009/0197825 | A1* | 8/2009 | Quart et al. | 514/46 |
| 2010/0081827 | A1 | 4/2010 | Girardet et al. | |
| 2011/0268801 | A1 | 11/2011 | Girardet et al. | |
| 2011/0293719 | A1 | 12/2011 | Girardet et al. | |
| 2012/0164222 | A1 | 6/2012 | Quart et al. | |
| 2012/0172405 | A1 | 7/2012 | Galvin et al. | |

FOREIGN PATENT DOCUMENTS

| WO | WO-2006-026356 | 3/2006 |
|---|---|---|
| WO | WO-2009-070740 | 6/2009 |
| WO | WO-2010-028190 | 3/2010 |

OTHER PUBLICATIONS

Kerr, B., et al. "Pharmacokinetics, Efficacy and Safety of Lesinurad, A Novel URAT1 Inhibitor, In Individuals with Mild to Moderate Renal Impairment" American College of Rheumatology Annual General Meeting, Nov. 5-9, 2011, Chicago.
Perez-Ruiz, F., et al. "Efficacy and Safety of Lesinurad (RDEA594), A Novel Uricosuric Agent, Given in Combination with Allopurinol in Allopurinol-Refractory Gout Patients: Randomized, Double-Blind, Placebo-Controlled, Phase 2B Study," Annual European Congress of Rheumatology EULAR 2011, May 25-28, 2011, London.
Perez-Ruiz, F., et al. "Efficacy and Safety of a Range of Doses RDEA594, a Novel Uricosuric Agent, as Monotherapy in Gout Patients: Randomized, Double-Blind, Placebo-Controlled, Phase 2 Experience," Annual European Congress of Rheumatology EULAR 2010, Jun. 16-19, 2010, Rome.
Sundy, J., et al. "Efficacy and Safety of Lesinurad (RDEA594), A Novel Uricosuric Agent, Given in Combination with Allopurinol in Allopurinol-Refractory Gout Patients: Preliminary Results from the Randomized, Blinded, Placebo-Controlled, Phase 2 B Extension Study," American College of Rheumatology Annual General Meeting, Nov. 9-11, 2011, Chicago.
Yeh, L., et al. , "Lesinurad (RDEA594), A Novel URAT1 Inhibitor, Shows Additive Serum Urate Lowering Effects in Combination with Xanthine Oxidase Inhibitor Febuxostat" International Society for the Study of Xenobiotics, 4th Asia Pacific ISSX Meeting, Apr. 22-25, 2011.
PCT/US11/067657 Search Report dated Jul. 18, 2012.
Fleishmann, R., et al. "Lesinurad (RDEA594), A Novel Uricosuric Agent, in Combination with Febuxostat Shows Significant Additive Urate Lowering Effects . . . " (May 25-28, 2011).
Kerr, B., et al. "Pharmacokinetics and Serum Urate Lowering Effect of RDEA594, A Novel URATI Inhibitor, In Gout Patients and Subjects with Varying . . . " (Mar. 2-5, 2011).
Lasko, B., et al. "RDEA594, a Novel Uricosuric Agent, Significantly Reduced Serum Urate Levels and Was Well Tolerated in a Phase 2a Pilot Study in . . . " (Oct. 16-21, 2009).
Perez-Ruiz, F., et al. "Efficacy and Safety of RDEA594, a Novel Uricosuric Agent, as Combination Therapy with Allopurinol in Gout Patients: Randomized, . . . " (Jun. 16-19, 2010).
Shen, Z., et al. "A RDEA594, A Novel Uricosuric Agent, Shows Significant Additive Activity in Combination with Allopurinol in Gout Patients" (Mar. 2-5, 2011).
Tan, P.K., et al. "Lesinurad (RDEA594), A Investigational Uricosuric Agent for Hyperuricemia and Gout, Blocks OAT4 Transport, Mechanism of . . . " (May 25-28, 2011).

(Continued)

*Primary Examiner* — Susannah Chung
(74) *Attorney, Agent, or Firm* — Wilson, Sonsini, Goodrich & Rosati

(57) ABSTRACT

Crystalline polymorphs and solid mesophase forms of sodium 2-(5-bromo-4-(4-cyclopropylnaphthalen-1-yl)-4H-1,2,4-triazol-3-ylthio)acetate are described. In addition, pharmaceutical compositions and uses of such compositions for the treatment of a variety of diseases and conditions are provided.

20 Claims, 15 Drawing Sheets

(56) References Cited

OTHER PUBLICATIONS

Yang, X., et al. "Evaluation of Drug-Drug Interaction Potential Between RDEA594, Allopurinol and Febuxostat in Preclinical Species" (Oct. 16-21, 2009).

Yeh, L., et al. "RDEA594, a Novel Uricosuric Agent, Shows Impressive Reductions in Serum Urate Levels as a Monotherapy and Substantial Additive Activity . . . " (Jun. 16-19, 2010).

Yeh, L., et al. "RDEA594, a Potential Uric Acid Lowering Agent through Inhibition of Uric Acid Reuptake, Shows Better Pharmacokinetics than its . . . " (Oct. 24-29, 2008).

Yeh, L., et al. "A Novel URAT1 Inhibitor, Shows Significant Additive Urate Lowering Effects in Combination with Febuxostat in Both Healthy Subjects and . . . " (Mar. 2-5, 2011).

Yeh, L.T., et al. "Mode of Action of RDEA594 as a Uric Acid Lowering Agent in Humans Following Multiple Doses of its Prodrug, RDEA806" (Jun. 11-14, 2008).

Yeh, L.T., et al. "Safety, Pharmacokinetics, and Serum Uric Acid Lowering Effect of RDEA594, a Novel, Uricosuric Agent, in Healthy Volunteers" (Jun. 10-13, 2009).

Yeh, L.-T., et al. "RDEA594:A Potent URAT1 Inhibitor Without Affecting Other Important Renal Transporters, OAT1 and OAT3" (Jun. 10-13, 2009).

PCT/US11/20233 Search Report dated Sep. 9, 2011.

EP 11732089 Search Report dated Jun. 6, 2013 (completed May 31, 2013).

\* cited by examiner

Sodium 2-(5-bromo-4-(4-cyclopropylnaphthalen-1-yl)-4H-1,2,4-triazol-3-ylthio)acetate,
Polymorph Form A: X-ray Powder Diffraction Pattern Sodium 2-(5-bromo-4-(4-cyclopropylnaphthalen-1-yl)-4H-1,2,4-triazol-3-ylthio)acetate,
Polymorph Form A: Differential Scanning Calorimetry Sodium 2-(5-bromo-4-(4-cyclopropylnaphthalen-1-yl)-4H-1,2,4-triazol-3-ylthio)acetate, Polymorph Form A: IR spectrum Sodium 2-(5-bromo-4-(4-cyclopropylnaphthalen-1-yl)-4H-1,2,4-triazol-3-ylthio)acetate,
Polymorph Form A: Raman spectrum Sodium 2-(5-bromo-4-(4-cyclopropylnaphthalen-1-yl)-4H-1,2,4-triazol-3-ylthio)acetate, Polymorph Form B: X-ray Powder Diffraction Pattern Sodium 2-(5-bromo-4-(4-cyclopropylnaphthalen-1-yl)-4H-1,2,4-triazol-3-ylthio)acetate, Polymorph Form B: Differential Scanning Calorimetry Sodium 2-(5-bromo-4-(4-cyclopropylnaphthalen-1-yl)-4H-1,2,4-triazol-3-ylthio)acetate, Polymorph Form B': X-ray Powder Diffraction Pattern Sodium 2-(5-bromo-4-(4-cyclopropylnaphthalen-1-yl)-4H-1,2,4-triazol-3-ylthio)acetate, Polymorph Form B': Differential Scanning Calorimetry Sodium 2-(5-bromo-4-(4-cyclopropylnaphthalen-1-yl)-4H-1,2,4-triazol-3-ylthio)acetate,
X-ray Powder Diffraction Pattern C Sodium 2-(5-bromo-4-(4-cyclopropylnaphthalen-1-yl)-4H-1,2,4-triazol-3-ylthio)acetate, X-ray Powder Diffraction Pattern D Sodium 2-(5-bromo-4-(4-cyclopropylnaphthalen-1-yl)-4H-1,2,4-triazol-3-ylthio)acetate,
X-ray Powder Diffraction Pattern E Sodium 2-(5-bromo-4-(4-cyclopropylnaphthalen-1-yl)-4H-1,2,4-triazol-3-ylthio)acetate, X-ray Powder Diffraction Mesophase Pattern 1

Sodium 2-(5-bromo-4-(4-cyclopropylnaphthalen-1-yl)-4H-1,2,4-triazol-3-ylthio)acetate, Cyclic Differential Scanning Calorimetry Mesophase Pattern 1

Sodium 2-(5-bromo-4-(4-cyclopropylnaphthalen-1-yl)-4H-1,2,4-triazol-3-ylthio)acetate,
X-ray Powder Diffraction Mesophase Pattern 2

Sodium 2-(5-bromo-4-(4-cyclopropylnaphthalen-1-yl)-4H-1,2,4-triazol-3-ylthio)acetate, X-ray Powder Diffraction Mesophase Pattern 3

POLYMORPHIC, CRYSTALLINE AND MESOPHASE FORMS OF SODIUM 2-(5-BROMO-4-(4-CYCLOPROPYLNAPH-THALEN-1-YL)-4H-1,2,4-TRIAZOL-3-YLTHIO) ACETATE, AND USES THEREOF

CROSS REFERENCE

This application is filed pursuant to 35 U.S.C. §371 as a United States National Phase Application of International Application Ser. No. PCT/US11/020233, filed Jan. 5, 2011, which claims the benefit of U.S. Provisional Application No. 61/293,602, filed Jan. 8, 2010 all of which are incorporated herein by reference in their entirety.

FIELD OF THE INVENTION

The present invention relates to polymorphic, crystalline and mesophase forms of sodium 2-(5-bromo-4-(4-cyclopropylnaphthalen-1-yl)-4H-1,2,4-triazol-3-ylthio)acetate, which decreases uric acid levels.

BACKGROUND OF THE INVENTION

Gout is associated with elevated levels of uric acid that crystallize and deposit in joints, tendons, and surrounding tissues. Gout is marked by recurrent attacks of red, tender, hot, and/or swollen joints.

SUMMARY OF THE INVENTION

Described herein are crystal polymorphs, mesophases, and other forms of sodium 2-(5-bromo-4-(4-cyclopropylnaphthalen-1-yl)-4H-1,2,4-triazol-3-ylthio)acetate:

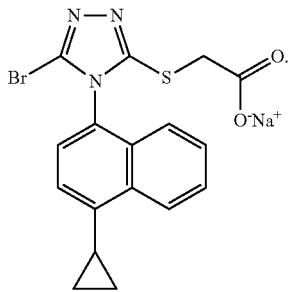

One aspect described herein are crystalline polymorphs of sodium 2-(5-bromo-4-(4-cyclopropylnaphthalen-1-yl)-4H-1,2,4-triazol-3-ylthio)acetate characterized by peaks at 4.90, 9.83, and 25.29°2θ±0.1°2θ. In further embodiment, such a crystalline polymorph is further characterized by at least two further peaks at 6.86, 8.41, 10.13, 17.92, and 23.10°2θ±0.1°2θ. In yet still further embodiments, the crystalline polymorph exhibits an x-ray powder diffraction pattern substantially the same as the x-ray powder diffraction pattern shown in FIG. 1. In a related aspect described herein are crystalline polymorphs of sodium 2-(5-bromo-4-(4-cyclopropylnaphthalen-1-yl)-4H-1,2,4-triazol-3-ylthio)acetate, characterized by an endothermic point onset, as determined by differential scanning calorimetry at about 62° C. In a further embodiment, the crystalline polymorph is characterized by a differential scanning calorimetry pattern substantially the same as the differential scanning calorimetry pattern shown in FIG. 2. In another related aspect described herein is the crystalline polymorph Form A. In a related aspect described herein are solid pharmaceutical compositions comprising an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form A, as an active ingredient; and at least one excipient or carrier. A method for treating or preventing hyperuricemia or a disease caused by elevated uric acid levels, comprising administering, to a subject in need, an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form A. A method for treating or preventing gout, comprising administering, to a subject in need, an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form A.

One aspect described herein are crystalline polymorphs of sodium 2-(5-bromo-4-(4-cyclopropylnaphthalen-1-yl)-4H-1,2,4-triazol-3-ylthio)acetate characterized by peaks at 4.22, 8.51, and 16.95°2θ±0.1°2θ. In further embodiment, such a crystalline polymorph is further characterized by a peak at 12.80°2θ±0.1°2θ. In yet still further embodiments, the crystalline polymorph exhibits an x-ray powder diffraction pattern substantially the same as the x-ray powder diffraction pattern shown in FIG. 5. In a related aspect described herein are crystalline polymorphs of sodium 2-(5-bromo-4-(4-cyclopropylnaphthalen-1-yl)-4H-1,2,4-triazol-3-ylthio)acetate, characterized by an endothermic point onset, as determined by differential scanning calorimetry at about 173° C. In a further embodiment, the crystalline polymorph is characterized by a differential scanning calorimetry pattern substantially the same as the differential scanning calorimetry pattern shown in FIG. 6. In another related aspect described herein is the crystalline polymorph Form B. In a related aspect described herein are solid pharmaceutical compositions comprising an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form B, as an active ingredient; and at least one excipient or carrier. A method for treating or preventing hyperuricemia or a disease caused by elevated uric acid levels, comprising administering, to a subject in need, an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form B. A method for treating or preventing gout, comprising administering, to a subject in need, an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form B.

One aspect described herein are crystalline polymorphs of sodium 2-(5-bromo-4-(4-cyclopropylnaphthalen-1-yl)-4H-1,2,4-triazol-3-ylthio)acetate characterized by an x-ray powder diffraction pattern substantially the same as the x-ray powder diffraction pattern shown in FIG. 7. In a related aspect described herein are crystalline polymorphs of sodium 2-(5- bromo-4-(4-cyclopropylnaphthalen-1-yl)-4H-1,2,4-triazol-3-ylthio)acetate, characterized by a differential scanning calorimetry pattern substantially the same as the differential scanning calorimetry pattern shown in FIG. 8. In another related aspect described herein is the crystalline polymorph Form B'. In a related aspect described herein are solid pharmaceutical compositions comprising an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form B', as an active ingredient; and at least one excipient or carrier. A method for treating or preventing hyperuricemia or a disease caused by elevated uric acid levels, comprising administering, to a subject in need, an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form B'. A method for treating or preventing gout, comprising administering, to a subject in need, an effective amount of the crystalline polymorph characterized by the aforementioned diffraction patterns, an effective amount of the crystalline polymorph characterized by the aforementioned differential scanning calorimetry patterns, or an effective amount of the crystalline polymorph Form B'.

One aspect described herein are crystalline polymorphs of sodium 2-(5-bromo-4-(4-cyclopropylnaphthalen-1-yl)-4H-1,2,4-triazol-3-ylthio)acetate characterized by peaks at 6.9, 10.1 and 22.6°2θ±0.1°2θ. In further embodiments, the crystalline polymorph is further characterized by at least two peaks at 23.3, 23.9, 25.2, 28.3 or 29.0°2θ±0.1°2θ. In yet still further embodiments, the crystalline polymorph exhibits an x-ray powder diffraction pattern substantially the same as the x-ray powder diffraction pattern shown in FIG. 9. In another related aspect described herein is the crystalline polymorph Form C. In a related aspect described herein are solid pharmaceutical compositions comprising an effective amount of the crystalline polymorph characterized by the aforementioned diffraction patterns, or an effective amount of the crystalline polymorph Form C, as an active ingredient; and at least one excipient or carrier. A method for treating or preventing hyperuricemia or a disease caused by elevated uric acid levels, comprising administering, to a subject in need, an effective amount of the crystalline polymorph characterized by the aforementioned diffraction patterns, or an effective amount of the crystalline polymorph Form C. A method for treating or preventing gout, comprising administering, to a subject in need, an effective amount of the crystalline polymorph characterized by the aforementioned diffraction patterns, or an effective amount of the crystalline polymorph Form C.

One aspect described herein are crystalline polymorphs of sodium 2-(5-bromo-4-(4-cyclopropylnaphthalen-1-yl)-4H-1,2,4-triazol-3-ylthio)acetate characterized by peaks at 10.3, 17.8 and 25.2°2θ±0.1°2θ. In yet still further embodiments, the crystalline polymorph exhibits an x-ray powder diffraction pattern substantially the same as the x-ray powder diffraction pattern shown in FIG. 10. In another related aspect described herein is the crystalline polymorph Form D. In a related aspect described herein are solid pharmaceutical compositions comprising an effective amount of the crystalline polymorph characterized by the aforementioned diffraction patterns, or an effective amount of the crystalline polymorph Form D, as an active ingredient; and at least one excipient or carrier. A method for treating or preventing hyperuricemia or a disease caused by elevated uric acid levels, comprising administering, to a subject in need, an effective amount of the crystalline polymorph characterized by the aforementioned diffraction patterns, or an effective amount of the crystalline polymorph Form D. A method for treating or preventing gout, comprising administering, to a subject in need, an effective amount of the crystalline polymorph characterized by the aforementioned diffraction patterns, or an effective amount of the crystalline polymorph Form D.

One aspect described herein are crystalline polymorphs of sodium 2-(5-bromo-4-(4-cyclopropylnaphthalen-1-yl)-4H-1,2,4-triazol-3-ylthio)acetate characterized by at least three peaks at 10.5, 22.9, 23.2 or 24.6°2θ±0.1°2θ. In yet still further embodiments, the crystalline polymorph exhibits an x-ray powder diffraction pattern substantially the same as the x-ray powder diffraction pattern shown in FIG. 11. In another related aspect described herein is the crystalline polymorph Form E. In a related aspect described herein are solid pharmaceutical compositions comprising an effective amount of the crystalline polymorph characterized by the aforementioned diffraction patterns, or an effective amount of the crystalline polymorph Form E, as an active ingredient; and at least one excipient or carrier. A method for treating or preventing hyperuricemia or a disease caused by elevated uric acid levels, comprising administering, to a subject in need, an effective amount of the crystalline polymorph characterized by the aforementioned diffraction patterns, or an effective amount of the crystalline polymorph Form E. A method for treating or preventing gout, comprising administering, to a subject in need, an effective amount of the crystalline polymorph characterized by the aforementioned diffraction patterns, or an effective amount of the crystalline polymorph Form E.

In further aspects are a solid mesophase form of sodium 2-(5-bromo-4-(4-cyclopropylnaphthalen-1-yl)-4H-1,2,4-triazol-3-ylthio)acetate, that exhibits an x-ray powder diffraction pattern substantially the same as the x-ray powder diffraction pattern shown in FIG. 12, FIG. 13, FIG. 14, or FIG. 15. In further embodiments are solid pharmaceutical compositions comprising an effective amount of any of the aforementioned solid mesophase forms of sodium 2-(5-bromo-4-(4-cyclopropylnaphthalen-1-yl)-4H-1,2,4-triazol-3-ylthio)acetate, or a combination thereof; and at least one excipient or carrier. In a further embodiments are methods for treating or preventing hyperuricemia or a disease caused by elevated uric acid levels, comprising administering an effective amount of any of the aforementioned solid mesophase forms, or a combination thereof. In a further embodiment are methods for treating or preventing gout, comprising administering an effective amount of any of the aforementioned solid mesophase forms, or a combination thereof.

In a further aspect are solid pharmaceutical compositions comprising an effective amount of at least two of the aforementioned crystalline polymorph or solid mesophase forms of sodium 2-(5-bromo-4-(4-cyclopropylnaphthalen-1-yl)-4H-1,2,4-triazol-3-ylthio)acetate; and at least one excipient or carrier.

In a further aspect are methods for treating or preventing hyperuricemia or a disease caused by elevated uric acid levels, comprising administering an effective amount of at least two of the aforementioned crystalline polymorph or solid mesophase forms of sodium 2-(5-bromo-4-(4-cyclopropylnaphthalen-1-yl)-4H-1,2,4-triazol-3-ylthio)acetate; and at least one excipient or carrier.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The present invention relates to polymorphic, crystalline and mesophase forms of sodium 2-(5-bromo-4-(4-cyclopropylnaphthalen-1-yl)-4H-1,2,4-triazol-3-ylthio)acetate, which decreases uric acid levels.

Figure 1:
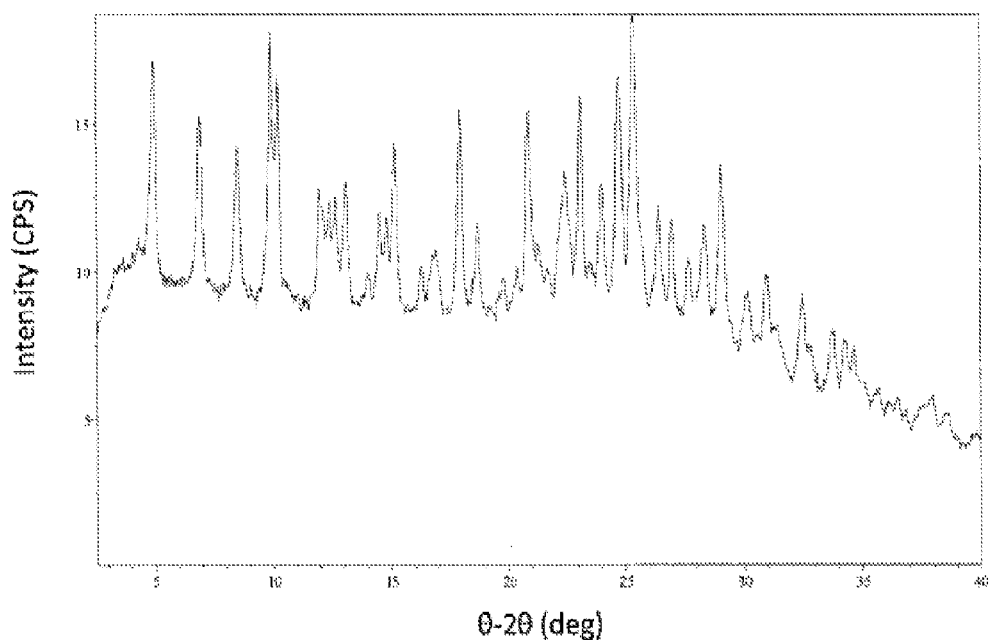
FIG. 1 represents an illustrative X-ray Powder Diffraction Pattern of Polymorph Form A.
Figure 2:
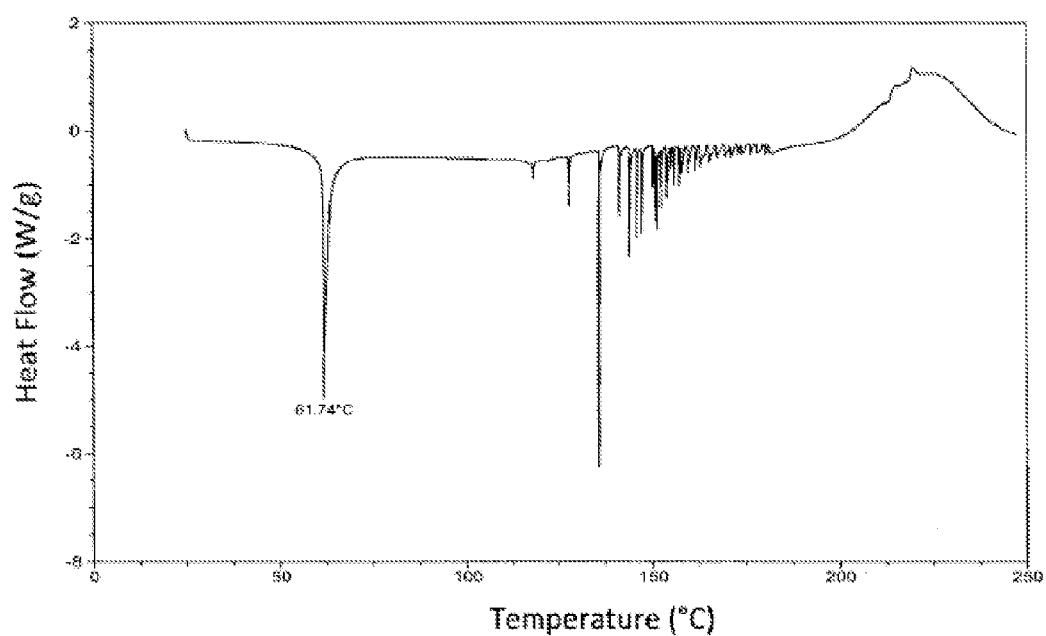
FIG. 2 represents an illustrative Differential Scanning calorimetry pattern of Polymorph Form A.

The term "polymorph Form A" refers to a crystalline form of sodium 2-(5-bromo-4-(4-cyclopropylnaphthalen-1-yl)-4H-1,2,4-triazol-3-ylthio)acetate that exhibits an x-ray powder diffraction pattern substantially the same as that shown in FIG. 1, and a differential scanning calorimetry profile substantially the same as that shown in FIG. 2.

Figure 5:
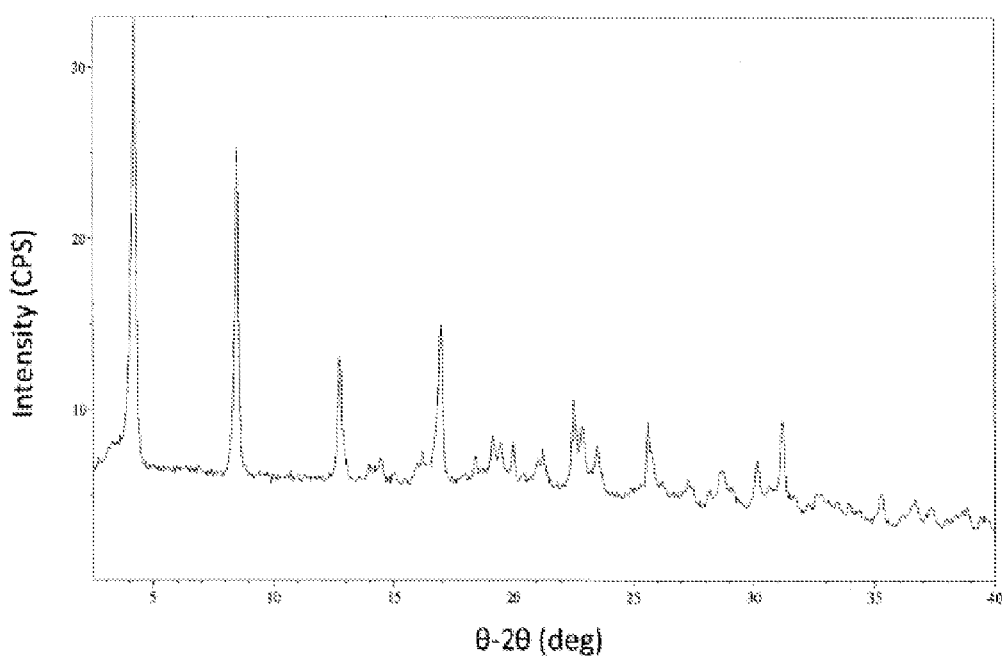
FIG. 5 represents an illustrative X-ray Powder Diffraction Pattern of Polymorph Form B.
Figure 6:
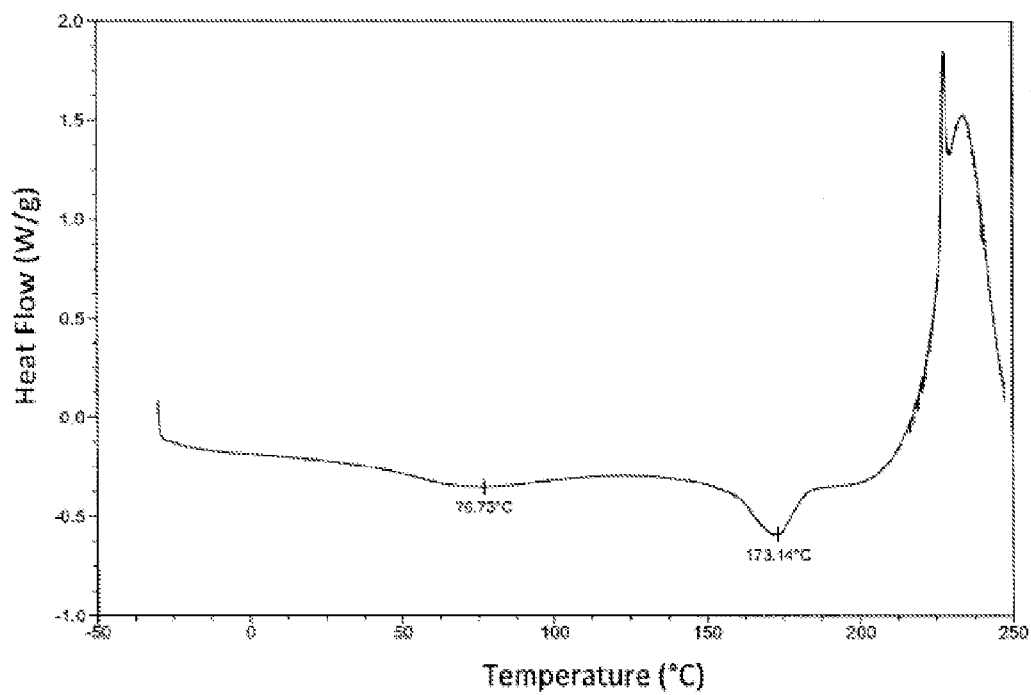
FIG. 6 represents an illustrative Differential Scanning calorimetry pattern of Polymorph Form B.

The term "polymorph Form B" refers to a crystalline form of sodium 2-(5-bromo-4-(4-cyclopropylnaphthalen-1-yl)-4H-1,2,4-triazol-3-ylthio)acetate that exhibits an x-ray powder diffraction pattern substantially the same as that shown in FIG. 5, and a differential scanning calorimetry profile substantially the same as that shown in FIG. 6.

Figure 7:
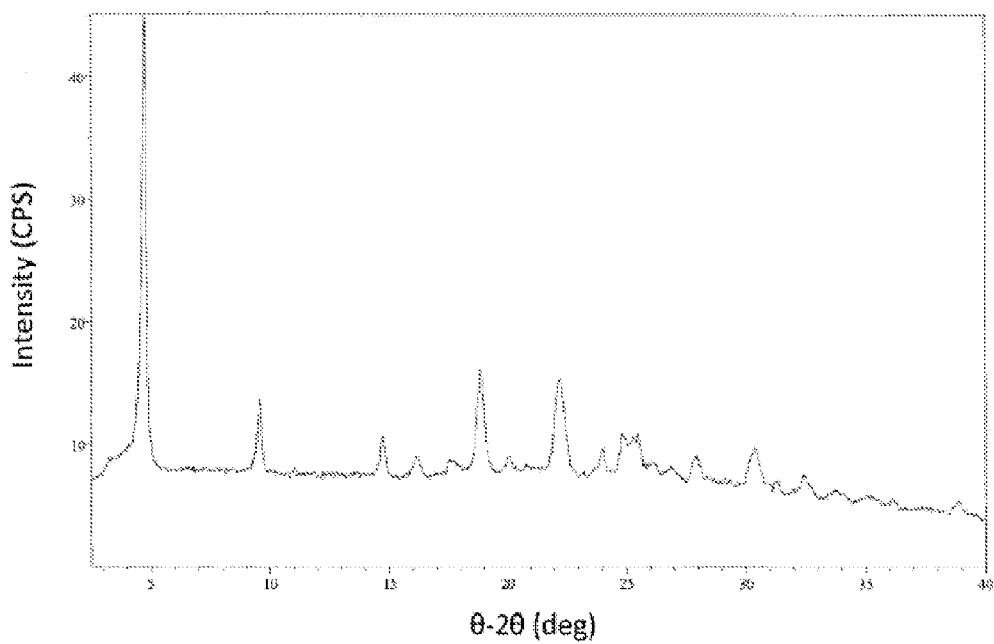
FIG. 7 represents an illustrative X-ray Powder Diffraction Pattern of Polymorph Form B'.
Figure 8:
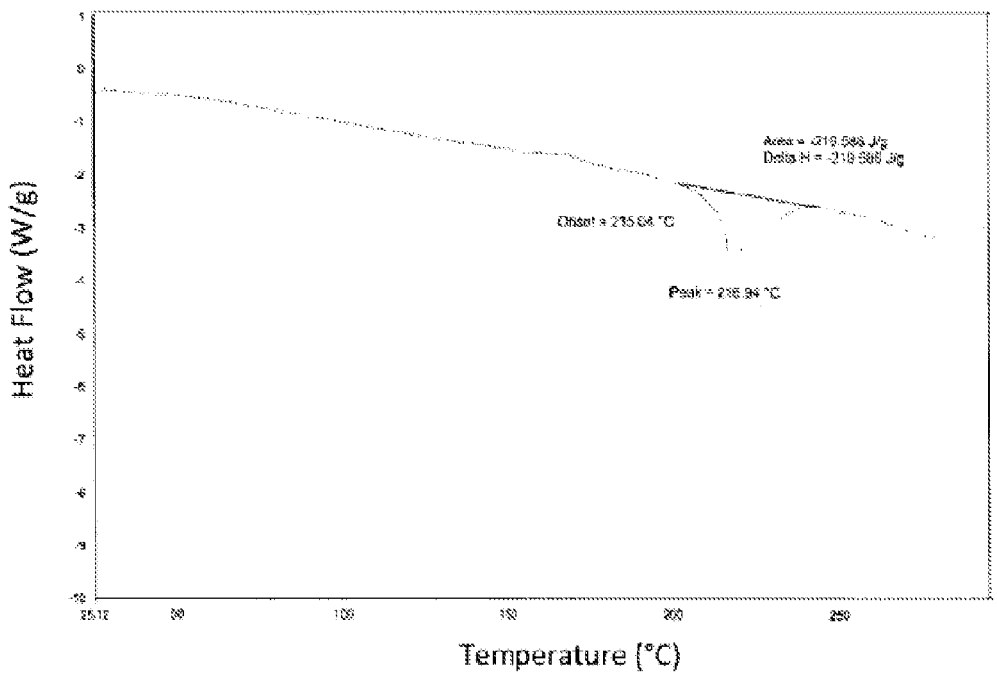
FIG. 8 represents an illustrative Differential Scanning calorimetry pattern of Polymorph Form B'.

The term "polymorph Form B'" refers to a crystalline form of sodium 2-(5-bromo-4-(4-cyclopropylnaphthalen-1-yl)-4H-1,2,4-triazol-3-ylthio)acetate that exhibits an x-ray powder diffraction pattern substantially the same as that shown in FIG. 7, and a differential scanning calorimetry profile substantially the same as that shown in FIG. 8.

Figure 9:
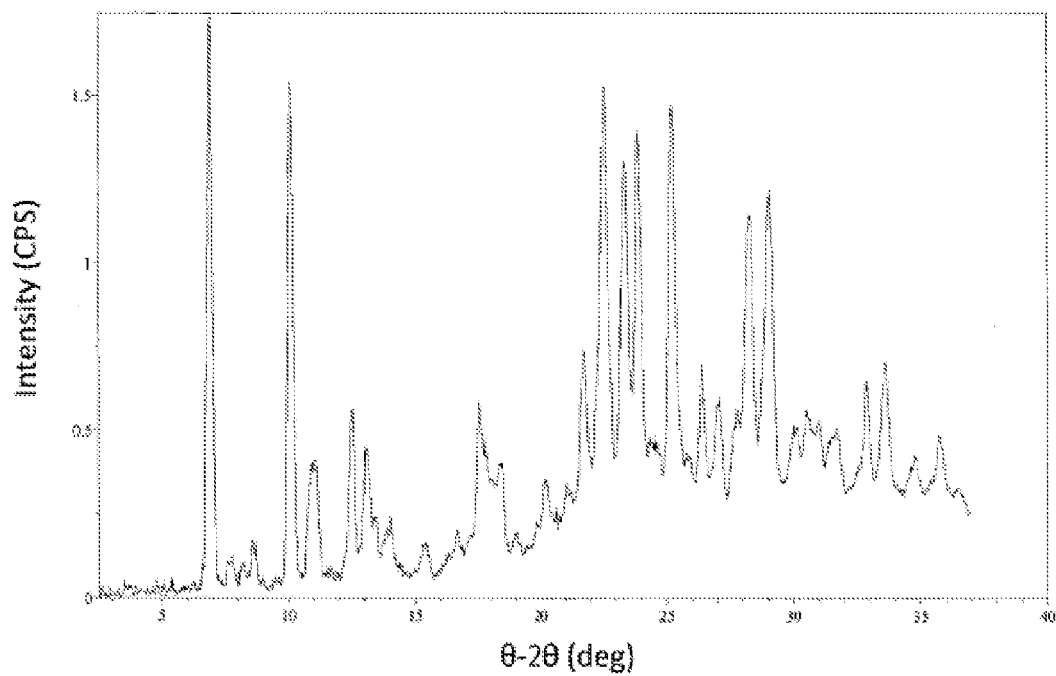
FIG. 9 represents an illustrative X-ray Powder Diffraction Pattern C.
Figure 10:
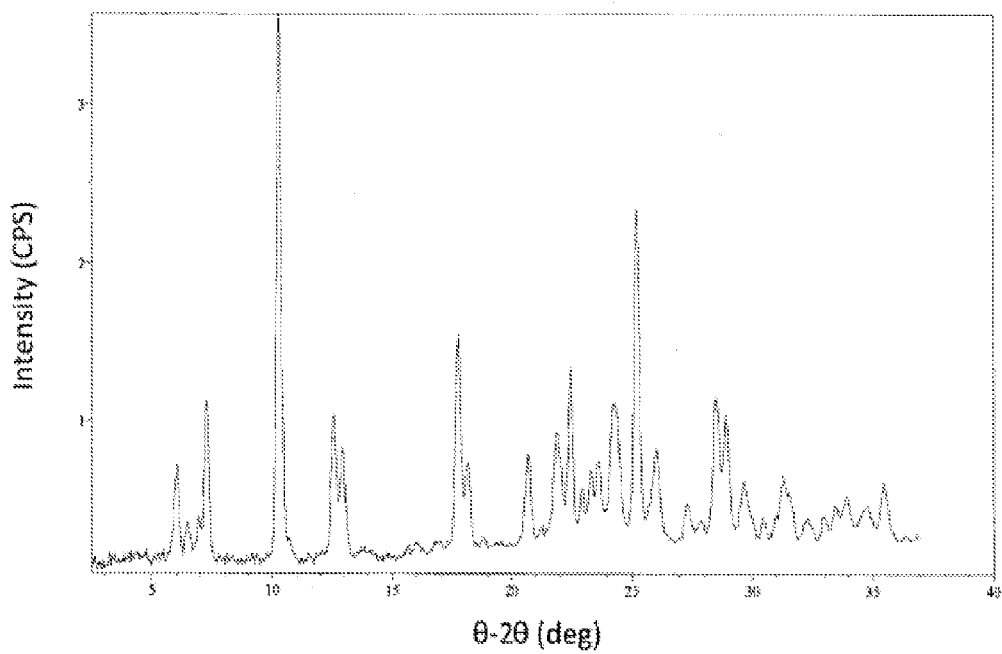
FIG. 10 represents an illustrative X-ray Powder Diffraction Pattern D.
Figure 11:
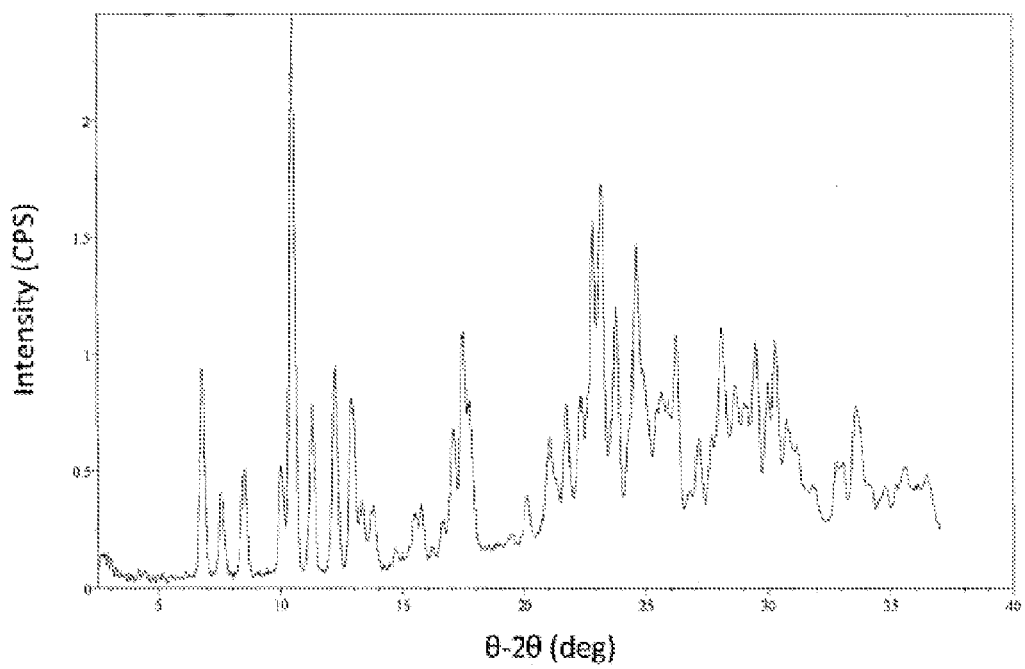
FIG. 11 represents an illustrative X-ray Powder Diffraction Pattern E.

Three other crystalline forms exhibit x-ray powder diffraction patterns C, D and E substantially the same as those shown in FIGS. 9, 10 and 11 respectively. Three solid mesophase forms 1, 2 and 3 exhibit x-ray powder diffraction patterns substantially the same as those shown in FIGS. 12, 14 and 15 respectively.

The present invention also relates to methods for treating or preventing diseases, comprising administering an effective amount of sodium 2-(5-bromo-4-(4-cyclopropylnaphthalen-1-yl)-4H-1,2,4-triazol-3-ylthio)acetate, as the crystalline polymorph Form A, the crystalline polymorph Form B, the crystalline polymorph Form B', the crystalline form displaying XRPD pattern C, the crystalline form displaying XRPD pattern D, the crystalline form displaying XRPD pattern E, the solid mesophase form 1, the solid mesophase form 2, the solid mesophase form 3 or a combination thereof.

The present invention also relates to solid pharmaceutical composition, comprising, as an active ingredient, an effective amount of sodium 2-(5-bromo-4-(4-cyclopropylnaphthalen-1-yl)-4H-1,2,4-triazol-3-ylthio)acetate, as the crystalline polymorph Form A, the crystalline polymorph Form B, the crystalline polymorph Form B', the crystalline form displaying XRPD pattern C, the crystalline form displaying XRPD pattern D, the crystalline form displaying XRPD pattern E, the solid mesophase form 1, the solid mesophase form 2, the solid mesophase form 3 or a combination thereof.

Also described are processes for the preparation of the crystalline polymorph Form A, the crystalline polymorph Form B, the crystalline polymorph Form B', the crystalline form displaying XRPD pattern C, the crystalline form displaying XRPD pattern D, the crystalline form displaying XRPD pattern E, the solid mesophase form 1, the solid mesophase form 2, the solid mesophase form 3 of sodium 2-(5-bromo-4-(4-cyclopropylnaphthalen-1-yl)-4H-1,2,4-triazol-3-ylthio)acetate.

In certain instances, the crystalline polymorphs of sodium 2-(5-bromo-4-(4-cyclopropylnaphthalen-1-yl)-4H-1,2,4-triazol-3-ylthio)acetate were found to exhibit increased stability in comparison to the amorphous solid state form of the carboxylic acid. In some instances, improved stability of the crystalline polymorphs of sodium 2-(5-bromo-4-(4-cyclopropylnaphthalen-1-yl)-4H-1,2,4-triazol-3-ylthio)acetate provides for the preparation of pharmaceutical dosage forms displaying reduced variability in the dosage present in a given dosage form, reduction in the presence of impurities in the final pharmaceutical product, and an improved shelf life of formulated dosage forms when compared to the pharmaceutical dosage form prepared with the amorphous solid state form of the carboxylic acid. In some embodiments, a polymorph described herein (e.g., Form A or Form B or Form B') demonstrates no degradation (e.g., less than 0.01%, less than 0.1%, less than 0.5% by wt.) (i) for at least 3 months under accelerated conditions (e.g., 40° C.-75% RH), for at least 4 months under accelerated conditions (e.g., 40° C.-75% RH), for at least 5 months under accelerated conditions (e.g., 40° C.-75% RH), for at least 6 months under accelerated conditions (e.g., 40° C.-75% RH), for at least 9 months under accelerated conditions (e.g., 40° C.-75% RH), for at least 12 months under accelerated conditions (e.g., 40° C.-75% RH), and/or (ii) for at least 12 months under long-term conditions (e.g., 25° C.-60% RH), for at least 18 months under long-term conditions (e.g., 25° C.-60% RH), for at least 24 months under long-term conditions (e.g., 25° C.-60% RH).

Sodium 2-(5-bromo-4-(4-cyclopropylnaphthalen-1-yl)-4H-1,2,4-triazol-3-ylthio)acetate Described herein are various polymorphic, crystalline and mesophase forms of sodium 2-(5-bromo-4-(4-cyclopropylnaphthalen-1-yl)-4H-1,2,4-triazol-3-ylthio)acetate which decreases uric acid levels, (see for example US patent publication 2009/0197825, US patent publication 2010/0056464 and US patent publication 2010/0056465). Details of clinical studies involving sodium 2-(5-bromo-4-(4-cyclopropylnaphthalen-1-yl)-4H-1,2,4-triazol-3-ylthio)acetate have been described in International patent application PCT/US2010/052958.

Polymorph Form A

In one embodiment, sodium 2-(5-bromo-4-(4-cyclopropylnaphthalen-1-yl)-4H-1,2,4-triazol-3-ylthio)acetate polymorph Form A exhibits an x-ray powder diffraction pattern characterized by the diffraction pattern summarized in Table 1A or Table 1B. In some embodiments, provided herein is a polymorph of sodium 2-(5-bromo-4-(4-cyclopropylnaphthalen-1-yl)-4H-1,2,4-triazol-3-ylthio)acetate comprising at least 3 peaks of ($\pm 0.1°2\theta$) of Table 1A or 1B. In certain embodiments, provided herein is a polymorph of sodium 2-(5-bromo-4-(4-cyclopropylnaphthalen-1-yl)-4H-1,2,4-triazol-3-ylthio)acetate comprising at least 4 peaks of ($\pm 0.1°2\theta$) of Table 1A or 1B, at least 5 peaks of ($\pm 0.1°2\theta$) of Table 1A or 1B, at least 6 peaks of ($\pm 0.1°2\theta$) of Table 1A or 1B, at least 8 peaks of ($\pm 0.1°2\theta$) of Table 1A or 1B, at least 10 peaks of ($\pm 0.1°2\theta$) of Table 1A, at least 15 peaks of ($\pm 0.1°2\theta$) of Table 1A, at least 20 peaks of ($\pm 0.1°2\theta$) of Table 1A, at least 25 peaks of ($\pm 0.1°2\theta$) of Table 1A, or at least 30 peaks of ($\pm 0.1°2\theta$) of Table 1A.

TABLE 1

| A | | | B | | |
|---|---|---|---|---|---|
| °2θ | d space (Å) | Intensity (%) | °2θ | d space (Å) | Intensity (%) |
| 4.90 ± 0.10 | 18.027 ± 0.375 | 71 | 4.90 ± 0.10 | 18.027 ± 0.375 | 71 |
| 6.86 ± 0.10 | 12.891 ± 0.191 | 100 | 6.86 ± 0.10 | 12.891 ± 0.191 | 100 |
| 8.41 ± 0.10 | 10.512 ± 0.126 | 61 | 8.41 ± 0.10 | 10.512 ± 0.126 | 61 |
| 9.83 ± 0.10 | 8.996 ± 0.092 | 63 | 9.83 ± 0.10 | 8.996 ± 0.092 | 63 |
| 10.13 ± 0.10 | 8.730 ± 0.087 | 97 | 10.13 ± 0.10 | 8.730 ± 0.087 | 97 |
| 10.60 ± 0.10 | 8.346 ± 0.079 | 16 | 17.92 ± 0.10 | 4.950 ± 0.028 | 70 |
| 11.92 ± 0.10 | 7.424 ± 0.063 | 45 | 23.10 ± 0.10 | 3.850 ± 0.017 | 55 |
| 12.32 ± 0.10 | 7.183 ± 0.059 | 45 | 25.29 ± 0.10 | 3.522 ± 0.014 | 68 |
| 12.57 ± 0.10 | 7.041 ± 0.056 | 45 | | | |
| 13.07 ± 0.10 | 6.772 ± 0.052 | 42 | | | |
| 14.01 ± 0.10 | 6.322 ± 0.045 | 21 | | | |
| 14.48 ± 0.10 | 6.118 ± 0.042 | 35 | | | |
| 14.80 ± 0.10 | 5.988 ± 0.041 | 23 | | | |
| 15.15 ± 0.10 | 5.850 ± 0.039 | 52 | | | |
| 16.28 ± 0.10 | 5.444 ± 0.033 | 18 | | | |
| 16.70 ± 0.10 | 5.309 ± 0.032 | 20 | | | |
| 16.90 ± 0.10 | 5.246 ± 0.031 | 22 | | | |
| 17.92 ± 0.10 | 4.950 ± 0.028 | 70 | | | |
| 18.64 ± 0.10 | 4.761 ± 0.025 | 36 | | | |
| 20.88 ± 0.10 | 4.255 ± 0.020 | 42 | | | |
| 21.35 ± 0.10 | 4.163 ± 0.019 | 25 | | | |
| 21.68 ± 0.10 | 4.099 ± 0.019 | 18 | | | |
| 22.42 ± 0.10 | 3.966 ± 0.018 | 38 | | | |
| 23.10 ± 0.10 | 3.850 ± 0.017 | 55 | | | |
| 23.54 ± 0.10 | 3.780 ± 0.016 | 20 | | | |
| 23.95 ± 0.10 | 3.715 ± 0.015 | 37 | | | |
| 24.67 ± 0.10 | 3.609 ± 0.014 | 44 | | | |
| 25.29 ± 0.10 | 3.522 ± 0.014 | 68 | | | |
| 26.38 ± 0.10 | 3.379 ± 0.013 | 33 | | | |
| 26.96 ± 0.10 | 3.307 ± 0.012 | 33 | | | |
| 27.63 ± 0.10 | 3.229 ± 0.012 | 22 | | | |
| 28.36 ± 0.10 | 3.147 ± 0.011 | 29 | | | |
| 29.07 ± 0.10 | 3.072 ± 0.010 | 35 | | | |

In one embodiment provided herein, the polymorph form A of sodium 2-(5-bromo-4-(4-cyclopropylnaphthalen-1-yl)-4H-1,2,4-triazol-3-ylthio)acetate is characterized by x-ray powder diffraction pattern peaks at 4.90, 9.83, and 25.29°2θ±0.1°2θ. In further embodiments, the polymorph form A is further characterized by at least one peak appearing at 6.86, 8.41, 10.13, 17.92, and 23.10°2θ±0.1°2θ. In further embodiments, the polymorph form A is further characterized by at least two peaks appearing at 6.86, 8.41, 10.13, 17.92, and 23.10°2θ±0.1°2θ. In yet still further embodiments, the polymorph exhibits an x-ray powder diffraction pattern substantially the same as the x-ray powder diffraction pattern shown in FIG. 1.

Polymorph Form B

In one embodiment, sodium 2-(5-bromo-4-(4-cyclopropylnaphthalen-1-yl)-4H-1,2,4-triazol-3-ylthio)acetate polymorph Form B exhibits an x-ray powder diffraction pattern characterized by the diffraction pattern summarized in Table 2A or 2B. In some embodiments, provided herein is a polymorph of sodium 2-(5-bromo-4-(4-cyclopropylnaphthalen-1-yl)-4H-1,2,4-triazol-3-ylthio)acetate comprising at least 2 peaks of (±0.1°2θ) of Table 2A or 2B. In certain embodiments, provided herein is a polymorph of sodium 2-(5-bromo-4-(4-cyclopropylnaphthalen-1-yl)-4H-1,2,4-triazol-3-ylthio)acetate comprising at least 3 peaks of (±0.1°2θ) of Table 2A or 2B, at least 4 peaks of (±0.1°2θ) of Table 2A or 2B, at least 5 peaks of (±0.1°2θ) of Table 2A, at least 6 peaks of (±0.1°2θ) of Table 2A, at least 8 peaks of (±0.1°2θ) of Table 2A, at least 10 peaks of (±0.1°2θ) of Table 2A, at least 12 peaks of (±0.1°2θ) of Table 2A, at least 14 peaks of (±0.1°2θ) of Table 2A, or at least 16 peaks of (±0.1°2θ) of Table 2A.

In one embodiment provided herein, the polymorph form B of sodium 2-(5-bromo-4-(4-cyclopropylnaphthalen-1-yl)-4H-1,2,4-triazol-3-ylthio)acetate is characterized by x-ray powder diffraction pattern peaks at 4.22, 8.51, and 16.95°2θ±0.1°2θ. In a further embodiment, the polymorph form B is further characterized by a peak appearing at 12.80°2θ±0.1°2θ. In yet still further embodiments, the polymorph exhibits an x-ray powder diffraction pattern substantially the same as the x-ray powder diffraction pattern shown in FIG. 5.

Polymorph Form B'

In one embodiment, sodium 2-(5-bromo-4-(4-cyclopropylnaphthalen-1-yl)-4H-1,2,4-triazol-3-ylthio)acetate polymorph Form B' exhibits an x-ray powder diffraction pattern characterized by the diffraction pattern summarized in FIG. 7.

Polymorph Form C

In one embodiment, sodium 2-(5-bromo-4-(4-cyclopropylnaphthalen-1-yl)-4H-1,2,4-triazol-3-ylthio)acetate polymorph Form C exhibits an x-ray powder diffraction pattern characterized by the diffraction pattern summarized in Table 3A or 3B. In some embodiments, provided herein is a polymorph of sodium 2-(5-bromo-4-(4-cyclopropylnaphthalen-1-yl)-4H-1,2,4-triazol-3-ylthio)acetate comprising at least 3 peaks of (±0.1°2θ) of Table 3A or 3B. In certain embodiments, provided herein is a polymorph of sodium 2-(5-bromo-4-(4-cyclopropylnaphthalen-1-yl)-4H-1,2,4-triazol-3-ylthio)acetate comprising at least 4 peaks of (±0.1°2θ) of Table 3A or 3B, at least 5 peaks of (±0.1°2θ) of Table 3A or 3B, at least 6 peaks of (±0.1°2θ) of Table 3A or 3B, at least 8 peaks of (±0.1°2θ) of Table 3A or 3B, at least 10 peaks of (±0.1°2θ) of Table 3A, at least 15 peaks of (±0.1°2θ) of Table 3A, at least 20 peaks of (±0.1°2θ) of Table 3A, or at least 25 peaks of (±0.1°2θ) of Table 3A.

TABLE 2

| A | | | B | | |
|---|---|---|---|---|---|
| °2θ | d space (Å) | Intensity (%) | °2θ | d space (Å) | Intensity (%) |
| 4.22 ± 0.10 | 20.939 ± 0.508 | 100 | 4.22 ± 0.10 | 20.939 ± 0.508 | 100 |
| 8.51 ± 0.10 | 10.392 ± 0.123 | 79 | 8.51 ± 0.10 | 10.392 ± 0.123 | 79 |
| 12.80 ± 0.10 | 6.917 ± 0.054 | 40 | 12.80 ± 0.10 | 6.917 ± 0.054 | 40 |
| 13.97 ± 0.10 | 6.337 ± 0.045 | 20 | 16.95 ± 0.10 | 5.231 ± 0.031 | 45 |
| 14.46 ± 0.10 | 6.126 ± 0.042 | 21 | | | |
| 16.19 ± 0.10 | 5.475 ± 0.034 | 23 | | | |
| 16.95 ± 0.10 | 5.231 ± 0.031 | 45 | | | |
| 18.40 ± 0.10 | 4.821 ± 0.026 | 22 | | | |
| 19.13 ± 0.10 | 4.639 ± 0.024 | 26 | | | |
| 19.48 ± 0.10 | 4.558 ± 0.023 | 24 | | | |
| 20.03 ± 0.10 | 4.433 ± 0.022 | 25 | | | |
| 21.28 ± 0.10 | 4.176 ± 0.019 | 23 | | | |
| 22.56 ± 0.10 | 3.942 ± 0.017 | 32 | | | |
| 22.90 ± 0.10 | 3.883 ± 0.017 | 27 | | | |
| 23.53 ± 0.10 | 3.781 ± 0.016 | 24 | | | |
| 25.64 ± 0.10 | 3.474 ± 0.013 | 28 | | | |
| 27.27 ± 0.10 | 3.271 ± 0.012 | 18 | | | |
| 28.17 ± 0.10 | 3.168 ± 0.011 | 15 | | | |
| 28.72 ± 0.10 | 3.108 ± 0.011 | 19 | | | |

TABLE 3

| A | | | B | | |
|---|---|---|---|---|---|
| °2θ | d space (Å) | Intensity (%) | °2θ | d space (Å) | Intensity (%) |
| 6.9 ± 0.1 | 12.774 ± 0.187 | 100 | 6.9 ± 0.1 | 12.774 ± 0.187 | 100 |
| 7.7 ± 0.1 | 11.512 ± 0.152 | 6 | 10.1 ± 0.1 | 8.758 ± 0.087 | 88 |
| 8.2 ± 0.1 | 10.809 ± 0.134 | 6 | 22.6 ± 0.1 | 3.941 ± 0.017 | 87 |
| 8.6 ± 0.1 | 10.306 ± 0.121 | 10 | 23.3 ± 0.1 | 3.811 ± 0.016 | 74 |
| 10.1 ± 0.1 | 8.758 ± 0.087 | 88 | 23.9 ± 0.1 | 3.726 ± 0.015 | 80 |
| 11.0 ± 0.1 | 8.014 ± 0.073 | 24 | 25.2 ± 0.1 | 3.534 ± 0.014 | 84 |
| 12.5 ± 0.1 | 7.059 ± 0.057 | 32 | 28.3 ± 0.1 | 3.158 ± 0.011 | 66 |
| 13.1 ± 0.1 | 6.779 ± 0.052 | 26 | 29.0 ± 0.1 | 3.075 ± 0.010 | 70 |
| 14.0 ± 0.1 | 6.308 ± 0.045 | 14 | | | |
| 15.4 ± 0.1 | 5.746 ± 0.037 | 10 | | | |
| 16.7 ± 0.1 | 5.315 ± 0.032 | 12 | | | |
| 17.6 ± 0.1 | 5.051 ± 0.029 | 34 | | | |
| 18.4 ± 0.1 | 4.827 ± 0.026 | 23 | | | |
| 19.1 ± 0.1 | 4.656 ± 0.024 | 11 | | | |
| 19.8 ± 0.1 | 4.480 ± 0.022 | 13 | | | |
| 20.2 ± 0.1 | 4.388 ± 0.022 | 20 | | | |
| 21.1 ± 0.1 | 4.215 ± 0.020 | 19 | | | |
| 21.8 ± 0.1 | 4.081 ± 0.019 | 42 | | | |
| 22.6 ± 0.1 | 3.941 ± 0.017 | 87 | | | |
| 23.3 ± 0.1 | 3.811 ± 0.016 | 74 | | | |
| 23.9 ± 0.1 | 3.726 ± 0.015 | 80 | | | |
| 25.2 ± 0.1 | 3.534 ± 0.014 | 84 | | | |
| 26.4 ± 0.1 | 3.376 ± 0.013 | 40 | | | |
| 27.1 ± 0.1 | 3.295 ± 0.012 | 34 | | | |
| 28.3 ± 0.1 | 3.158 ± 0.011 | 66 | | | |
| 29.0 ± 0.1 | 3.075 ± 0.010 | 70 | | | |

In one embodiment provided herein, the polymorph form C of sodium 2-(5-bromo-4-(4-cyclopropylnaphthalen-1-yl)-4H-1,2,4-triazol-3-ylthio)acetate is characterized by x-ray powder diffraction pattern peaks at 6.9, 10.1, and 22.6°2θ±0.1°2θ. In further embodiments, the polymorph form C is further characterized by at least one peak appearing at 23.3, 23.9, 25.2, 28.3, and 29.0°2θ±0.1°2θ. In further embodiments, the polymorph form C is further characterized by at least two peaks appearing at 23.3, 23.9, 25.2, 28.3, and 29.0°2θ±0.1°2θ. In yet still further embodiments, the polymorph exhibits an x-ray powder diffraction pattern substantially the same as the x-ray powder diffraction pattern shown in FIG. 9.

Polymorph Form D

In one embodiment, sodium 2-(5-bromo-4-(4-cyclopropylnaphthalen-1-yl)-4H-1,2,4-triazol-3-ylthio)acetate polymorph Form D exhibits an x-ray powder diffraction pattern characterized by the diffraction pattern summarized in Table 4A or 4B. In some embodiments, provided herein is a polymorph of sodium 2-(5-bromo-4-(4-cyclopropylnaphthalen-1-yl)-4H-1,2,4-triazol-3-ylthio)acetate comprising at least 2 peaks of (±0.1°2θ) of Table 4A or 4B. In certain embodiments, provided herein is a polymorph of sodium 2-(5-bromo-4-(4-cyclopropylnaphthalen-1-yl)-4H-1,2,4-triazol-3-ylthio)acetate comprising at least 3 peaks of (±0.1°2θ) of Table 3A or 3B, at least 4 peaks of (±0.1°2θ) of Table 3A, at least 5 peaks of (±0.1°2θ) of Table 3A, at least 6 peaks of (±0.1°2θ) of Table 3A, at least 8 peaks of (±0.1°2θ) of Table 3A, at least 10 peaks of (±0.1°2θ) of Table 3A, at least 15 peaks of (±0.1°2θ) of Table 3A, or at least 20 peaks of (±0.1°2θ) of Table 3A.

TABLE 4

| A | | | B | | |
|---|---|---|---|---|---|
| °2θ | d space (Å) | Intensity (%) | °2θ | d space (Å) | Intensity (%) |
| 6.1 ± 0.1 | 14.585 ± 0.244 | 20 | 10.3 ± 0.1 | 8.605 ± 0.084 | 100 |
| 6.5 ± 0.1 | 13.599 ± 0.212 | 10 | 17.8 ± 0.1 | 4.994 ± 0.028 | 43 |
| 6.9 ± 0.1 | 12.737 ± 0.186 | 11 | 25.2 ± 0.1 | 3.531 ± 0.014 | 66 |
| 7.3 ± 0.1 | 12.177 ± 0.170 | 31 | | | |
| 10.3 ± 0.1 | 8.605 ± 0.084 | 100 | | | |
| 12.6 ± 0.1 | 7.048 ± 0.056 | 29 | | | |
| 12.9 ± 0.1 | 6.842 ± 0.053 | 23 | | | |
| 17.8 ± 0.1 | 4.994 ± 0.028 | 43 | | | |
| 18.1 ± 0.1 | 4.896 ± 0.027 | 21 | | | |
| 20.7 ± 0.1 | 4.287 ± 0.021 | 22 | | | |
| 21.9 ± 0.1 | 4.062 ± 0.018 | 26 | | | |
| 22.5 ± 0.1 | 3.959 ± 0.017 | 38 | | | |
| 23.0 ± 0.1 | 3.874 ± 0.017 | 16 | | | |
| 23.3 ± 0.1 | 3.815 ± 0.016 | 20 | | | |
| 23.6 ± 0.1 | 3.764 ± 0.016 | 21 | | | |
| 24.3 ± 0.1 | 3.663 ± 0.015 | 31 | | | |
| 25.2 ± 0.1 | 3.531 ± 0.014 | 66 | | | |
| 26.0 ± 0.1 | 3.425 ± 0.013 | 23 | | | |
| 27.3 ± 0.1 | 3.267 ± 0.012 | 14 | | | |
| 27.9 ± 0.1 | 3.198 ± 0.011 | 11 | | | |
| 28.5 ± 0.1 | 3.132 ± 0.011 | 32 | | | |
| 28.9 ± 0.1 | 3.087 ± 0.010 | 29 | | | |
| 29.7 ± 0.1 | 3.012 ± 0.010 | 18 | | | |

In one embodiment provided herein, the polymorph form D of sodium 2-(5-bromo-4-(4-cyclopropylnaphthalen-1-yl)-4H-1,2,4-triazol-3-ylthio)acetate is characterized by x-ray powder diffraction pattern peaks at 10.3, 17.8, and 25.2°2θ±0.1°2θ. In yet still further embodiments, the polymorph exhibits an x-ray powder diffraction pattern substantially the same as the x-ray powder diffraction pattern shown in FIG. 10.

Polymorph Form E

In one embodiment, sodium 2-(5-bromo-4-(4-cyclopropylnaphthalen-1-yl)-4H-1,2,4-triazol-3-ylthio)acetate polymorph Form E exhibits an x-ray powder diffraction pattern characterized by the diffraction pattern summarized in Table 5. In some embodiments, provided herein is a polymorph of sodium 2-(5-bromo-4-(4-cyclopropylnaphthalen-1-yl)-4H-1,2,4-triazol-3-ylthio)acetate comprising at least 2 peaks of (±0.1°2θ) of Table 5A or 5B. In certain embodiments, provided herein is a polymorph of sodium 2-(5-bromo-4-(4-cyclopropylnaphthalen-1-yl)-4H-1,2,4-triazol-3-ylthio)acetate comprising at least 3 peaks of (±0.1°2θ) of Table 5A or 5B, at least 4 peaks of (±0.1°2θ) of Table 5A or 5B, at least 5 peaks of (±0.1°2θ) of Table 5A or 5B, at least 6 peaks of (±0.1°2θ) of Table 5A or 5B, at least 8 peaks of (±0.1°2θ) of Table 5A or 5B, at least 10 peaks of (±0.1°2θ) of Table 5A, at least 15 peaks of (±0.1°2θ) of Table 5A, at least 20 peaks of (±0.1°2θ) of Table 5A, at least 25 peaks of (±0.1°2θ) of Table 5A, or at least 30 peaks of (±0.1°2θ) of Table 5A.

TABLE 5

| A | | | B | | |
|---|---|---|---|---|---|
| °2θ | d space (Å) | Intensity (%) | °2θ | d space (Å) | Intensity (%) |
| 6.8 ± 0.1 | 13.038 ± 0.195 | 38 | 10.5 ± 0.1 | 8.425 ± 0.081 | 100 |
| 7.6 ± 0.1 | 11.694 ± 0.157 | 17 | 22.9 ± 0.1 | 3.890 ± 0.017 | 64 |
| 8.5 ± 0.1 | 10.378 ± 0.123 | 20 | 23.2 ± 0.1 | 3.834 ± 0.016 | 70 |
| 10.0 ± 0.1 | 8.828 ± 0.089 | 21 | 24.6 ± 0.1 | 3.616 ± 0.015 | 60 |
| 10.5 ± 0.1 | 8.425 ± 0.081 | 100 | | | |
| 11.3 ± 0.1 | 7.844 ± 0.070 | 32 | | | |
| 12.2 ± 0.1 | 7.243 ± 0.060 | 38 | | | |
| 12.9 ± 0.1 | 6.863 ± 0.053 | 33 | | | |
| 13.3 ± 0.1 | 6.647 ± 0.050 | 15 | | | |
| 13.8 ± 0.1 | 6.417 ± 0.047 | 14 | | | |
| 14.7 ± 0.1 | 6.026 ± 0.041 | 7 | | | |
| 15.5 ± 0.1 | 5.724 ± 0.037 | 13 | | | |
| 15.8 ± 0.1 | 5.623 ± 0.036 | 15 | | | |
| 16.2 ± 0.1 | 5.471 ± 0.034 | 7 | | | |
| 16.6 ± 0.1 | 5.328 ± 0.032 | 11 | | | |
| 17.1 ± 0.1 | 5.198 ± 0.030 | 28 | | | |
| 17.5 ± 0.1 | 5.068 ± 0.029 | 45 | | | |
| 19.4 ± 0.1 | 4.566 ± 0.023 | 9 | | | |
| 20.2 ± 0.1 | 4.405 ± 0.022 | 16 | | | |
| 21.1 ± 0.1 | 4.215 ± 0.020 | 26 | | | |
| 21.8 ± 0.1 | 4.081 ± 0.019 | 32 | | | |
| 22.4 ± 0.1 | 3.973 ± 0.018 | 33 | | | |
| 22.9 ± 0.1 | 3.890 ± 0.017 | 64 | | | |
| 23.2 ± 0.1 | 3.834 ± 0.016 | 70 | | | |
| 23.8 ± 0.1 | 3.739 ± 0.016 | 49 | | | |
| 24.6 ± 0.1 | 3.616 ± 0.015 | 60 | | | |
| 25.7 ± 0.1 | 3.472 ± 0.013 | 34 | | | |
| 26.2 ± 0.1 | 3.396 ± 0.013 | 44 | | | |
| 27.2 ± 0.1 | 3.283 ± 0.012 | 26 | | | |
| 28.1 ± 0.1 | 3.176 ± 0.011 | 45 | | | |
| 28.7 ± 0.1 | 3.115 ± 0.011 | 35 | | | |
| 29.1 ± 0.1 | 3.071 ± 0.010 | 32 | | | |
| 29.5 ± 0.1 | 3.028 ± 0.010 | 43 | | | |
| 30.0 ± 0.1 | 2.979 ± 0.010 | 36 | | | |

In one embodiment provided herein, the polymorph form E of sodium 2-(5-bromo-4-(4-cyclopropylnaphthalen-1-yl)-4H-1,2,4-triazol-3-ylthio)acetate is characterized by x-ray powder diffraction pattern peaks at 10.5, 22.9, 23.2, and 24.6°2θ±0.1°2θ. In yet still further embodiments, the polymorph exhibits an x-ray powder diffraction pattern substantially the same as the x-ray powder diffraction pattern shown in FIG. 11.

In certain embodiments, any of the polymorphs described herein (e.g., Form A) optionally comprises (or is intermixed or in combination with) a certain amount of amorphous sodium 2-(5-bromo-4-(4-cyclopropylnaphthalen-1-yl)-4H-1,2,4-triazol-3-ylthio)acetate. In some embodiments, the amorphous component of the polymorph (e.g., Form A) or polymorph combination comprises less than 50 wt. % of the polymorph or polymorph combination, less than 25 wt. % of the polymorph or polymorph combination, less than 15 wt. % of the polymorph or polymorph combination, less than 10 wt. % of the polymorph or polymorph combination, or less than 5 wt. % of the polymorph or polymorph combination.

Hydrates

In certain embodiments, provided herein is a sodium 2-(5-bromo-4-(4-cyclopropylnaphthalen-1-yl)-4H-1,2,4-triazol-3-ylthio)acetate hydrate. In some embodiments, provided herein the sodium 2-(5-bromo-4-(4-cyclopropylnaphthalen-1-yl)-4H-1,2,4-triazol-3-ylthio)acetate hydrate is crystalline. In still further embodiments, the crystalline 2-(5-bromo-4-(4-cyclopropylnaphthalen-1-yl)-4H-1,2,4-triazol-3-ylthio)acetate hydrate comprises 2-(5-bromo-4-(4-cyclopropylnaphthalen-1-yl)-4H-1,2,4-triazol-3-ylthio)acetate and water in a mol ratio of between 1:1 to 1:5. In some embodiments, the crystalline 2-(5-bromo-4-(4-cyclopropylnaphthalen-1-yl)-4H-1,2,4-triazol-3-ylthio)acetate hydrate comprises 2-(5-bromo-4-(4-cyclopropylnaphthalen-1-yl)-4H-1,2,4-triazol-3-ylthio)acetate and water in a mol ratio of between 1:1.5 and 1:3.5, or between 1:1.8 to 1:3, or between 1:2 and 1:2.8, or about 1:2, or about 1:2.5. In some embodiments, provided herein is a sodium 2-(5-bromo-4-(4-cyclopropylnaphthalen-1-yl)-4H-1,2,4-triazol-3-ylthio)acetate hydrate comprising at least 5 wt. % water. In certain embodiments, provided herein is a sodium 2-(5-bromo-4-(4-cyclopropylnaphthalen-1-yl)-4H-1,2,4-triazol-3-ylthio)acetate hydrate comprising at least 9 wt. % water, 9-15 wt. % water, 10-13 wt. % water, 5-25 wt. % water, or the like.

Particle Size

In certain embodiments, provided herein is a sodium 2-(5-bromo-4-(4-cyclopropylnaphthalen-1-yl)-4H-1,2,4-triazol-3-ylthio)acetate polymorph particle (e.g., crystalline, or comprising a crystalline component). In some embodiments, provided herein is a sodium 2-(5-bromo-4-(4-cyclopropylnaphthalen-1-yl)-4H-1,2,4-triazol-3-ylthio)acetate polymorph (e.g., crystalline, or comprising a crystalline component) having a particle size of about 5-50 microns. In some embodiments, the average particle size is at least 10 microns, 15-50 microns, 15-35 microns, 35-45 microns, 35-40 microns, about 40 microns, or the like. In some embodiments, particles of sodium 2-(5-bromo-4-(4-cyclopropylnaphthalen-1-yl)-4H-1,2,4-triazol-3-ylthio)acetate (e.g., crystalline, or comprising a crystalline component, such as a polymorph of Form A) having an average diameter of greater than 5 or 10 microns have improved stability parameters compared to smaller diameters. In some embodiments, provided herein or used in any composition or method described herein is a sodium 2-(5-bromo-4-(4-cyclopropylnaphthalen-1-yl)-4H-1,2,4-triazol-3-ylthio)acetate polymorph that is not micronized.

Uric acid is the result of the oxidation of xanthine. Disorders of uric acid metabolism include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

DEFINITIONS

The term "subject", as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "effective amount", "therapeutically effective amount" or "pharmaceutically effective amount" as used herein, refer to an amount of at least one agent or compound being administered that is sufficient to treat or prevent the particular disease or condition. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The term "substantially the same as" as used herein, refers to a powder x-ray diffraction pattern or differential scanning calorimetry pattern that may be non-identical to those depicted herein, but that falls within the limits of experimental error, when considered by one of ordinary skill in the art.

"Representative Peaks" are the prominent peaks of an x-ray powder diffraction pattern. Note that prominent peaks are identified only if multiple XRPD patterns from multiple diffractometers are available and the effects of both particle statistics (reproducibility among XRPD patterns) and preferred orientation (consistency of relative intensity among XRPD patterns) are negligible.

"Characteristic peaks" are a subset of Representative Peaks and are used to differentiate one crystalline polymorph or form from another crystalline polymorph or form. Characteristic peaks may be determined by evaluating which representative peaks, if any, are present in one crystalline polymorph of a compound against all other known crystalline polymorphs of that compound. Not all crystalline polymorphs of a compound necessarily have at least one characteristic peak.

Modulating URAT-1 Activity

The invention also relates to methods of modulating URAT-1 activity by contacting URAT-1 with an amount of a polymorphic, crystalline or mesophase form of sodium 2-(5-bromo-4-(4-cyclopropylnaphthalen-1-yl)-4H-1,2,4-triazol-3-ylthio)acetate, as described herein, sufficient to modulate the activity of URAT-1. Modulate can be inhibiting or activating URAT-1 activity. In some embodiments, the invention provides methods of inhibiting URAT-1 activity by contacting URAT-1 with an amount of a polymorphic, crystalline or mesophase form of sodium 2-(5-bromo-4-(4-cyclopropyl-naphthalen-1-yl)-4H-1,2,4-triazol-3-ylthio)acetate, as described herein, sufficient to inhibit the activity of URAT-1. In some embodiments, the invention provides methods of inhibiting URAT-1 activity in a solution by contacting said solution with an amount of a polymorphic, crystalline or mesophase form of sodium 2-(5-bromo-4-(4-cyclopropyl-naphthalen-1-yl)-4H-1,2,4-triazol-3-ylthio)acetate, as described herein sufficient to inhibit the activity of URAT-1 in said solution. In some embodiments, the invention provides methods of inhibiting URAT-1 activity in a cell by contacting said cell with an amount of a polymorphic, crystalline or mesophase form of sodium 2-(5-bromo-4-(4-cyclopropyl-naphthalen-1-yl)-4H-1,2,4-triazol-3-ylthio)acetate, as described herein, sufficient to inhibit the activity of URAT-1 in said cell. In some embodiments, the invention provides methods of inhibiting URAT-1 activity in a tissue by contacting said tissue with an amount of a polymorphic, crystalline or mesophase form of sodium 2-(5-bromo-4-(4-cyclopropyl-naphthalen-1-yl)-4H-1,2,4-triazol-3-ylthio)acetate, as described herein, sufficient to inhibit the activity of URAT-1 in said tissue. In some embodiments, the invention provides methods of inhibiting URAT-1 activity in blood by contacting the blood with an amount of a polymorphic, crystalline or mesophase form of sodium 2-(5-bromo-4-(4-cyclopropyl-naphthalen-1-yl)-4H-1,2,4-triazol-3-ylthio)acetate, as described herein, sufficient to inhibit the activity of URAT-1 in blood. In some embodiments, the invention provides methods of inhibiting URAT-1 activity in plasma by contacting the plasma with an amount of a polymorphic, crystalline or mesophase form of sodium 2-(5-bromo-4-(4-cyclopropyl-naphthalen-1-yl)-4H-1,2,4-triazol-3-ylthio)acetate, as described herein, sufficient to inhibit the activity of URAT-1 in plasma. In some embodiments, the invention provides methods of inhibiting URAT-1 activity in an animal by contacting said animal with an amount of a polymorphic, crystalline or mesophase form of sodium 2-(5-bromo-4-(4-cyclo-propylnaphthalen-1-yl)-4H-1,2,4-triazol-3-ylthio)acetate, as described herein sufficient to inhibit the activity of URAT-1 in said animal. In some embodiments, the invention provides methods of inhibiting URAT-1 activity in a mammal by contacting said mammal with an amount of a polymorphic, crystalline or mesophase form of sodium 2-(5-bromo-4-(4-cyclo-propylnaphthalen-1-yl)-4H-1,2,4-triazol-3-ylthio)acetate, as described herein sufficient to inhibit the activity of URAT-1 in said mammal. In some embodiments, the invention provides methods of inhibiting URAT-1 activity in a human by contacting said human with an amount of a polymorphic, crystalline or mesophase form of sodium 2-(5-bromo-4-(4-cyclo-propylnaphthalen-1-yl)-4H-1,2,4-triazol-3-ylthio)acetate, as described herein, sufficient to inhibit the activity of URAT-1 in said human.

Pharmaceutical Compositions

Described herein are pharmaceutical compositions comprising an effective amount of a polymorphic, crystalline or mesophase form of sodium 2-(5-bromo-4-(4-cyclopropyl-naphthalen-1-yl)-4H-1,2,4-triazol-3-ylthio)acetate, as described herein. In some embodiments, the pharmaceutical compositions comprise an effective amount of a polymorphic, crystalline or mesophase form of sodium 2-(5-bromo-4-(4-cyclopropylnaphthalen-1-yl)-4H-1,2,4-triazol-3-ylthio)acetate, as described herein, and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human. In some embodiments the pharmaceutical compositions are for the treatment or prophylaxis of disorders of uric acid metabolism. In some embodiments the pharmaceutical compositions are for the treatment or prophylaxis of hyperuricemia. In some embodiments the pharmaceutical compositions are for the treatment or prophylaxis of gout.

Modes of Administration, Formulations and Dosage Forms

Described herein are pharmaceutical compositions comprising a polymorphic, crystalline or mesophase form of sodium 2-(5-bromo-4-(4-cyclopropylnaphthalen-1-yl)-4H-1,2,4-triazol-3-ylthio)acetate, as described herein. The compound, compound forms and compositions described herein may be administered either alone or in combination with pharmaceutically acceptable carriers, excipients or diluents, in a pharmaceutical composition, according to standard pharmaceutical practice. Administration can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. Those of skill in the art will be familiar with administration techniques that can be employed with the compounds and methods of the invention. By way of example only, the compounds, compound forms and compositions described herein can be administered locally to the area in need of treatment, by for example, local infusion during surgery, topical application such as creams or ointments, injection, catheter, or implant, said implant made for example, out of a porous, non-porous, or gelatinous material, including membranes, such as sialastic membranes, or fibers. The administration can also be by direct injection at the site of a diseased tissue or organ.

The pharmaceutical compositions described herein may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

The formulations may conveniently be presented in unit dosage form and may be prepared by any of the methods in the art of pharmacy. All methods include the step of bringing into association a compound or compound form of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Methods of preparing various pharmaceutical compositions with a specific amount of active compound are known, or will be apparent, to those skilled in this art.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician.

Also, the route of administration may vary depending on the condition and its severity. The pharmaceutical composition may be in unit dosage form. In such form, the preparation is subdivided into unit doses containing appropriate quantities of the active component, e.g., an effective amount to achieve the desired purpose. Determination of the proper dosage for a particular situation is within the skill of the art. For convenience, the total daily dosage may be divided and administered in portions during the day if desired. The amount and frequency of administration will be regulated according to the judgment of the attending clinician (physician) considering such factors as described above. Thus the amount of pharmaceutical composition to be administered may vary widely. Administration may occur in an amount of between about 0.001 mg/kg of body weight to about 100 mg/kg of body weight per day (administered in single or divided doses), or at least about 0.1 mg/kg of body weight per day. A particular therapeutic dosage can include, e.g., from about 0.01 mg to about 7000 mg of compound, or, e.g., from about 0.05 mg to about 2500 mg. In other embodiments a particular therapeutic dosage is selected from about 200 mg, about 300 mg, about 400 mg, about 500 mg, about 600 mg, or about 700 mg. The quantity of active compound in a unit dose of preparation may be varied or adjusted from about 0.1 mg to 1000 mg, from about 1 mg to 300 mg, or 10 mg to 200 mg, according to the particular application. In other embodiments a particular unit dosage is selected from 100 mg, 200 mg or 300 mg. In some instances, dosage levels below the lower limit of the aforesaid range may be more than adequate, while in other cases still larger doses may be employed without causing any harmful side effect, e.g. by dividing such larger doses into several small doses for administration throughout the day. In combinational applications in which the compound is not the sole therapy, it may be possible to administer lesser amounts of compound and still have therapeutic or prophylactic effect.

Combination Therapies

The compounds and compound forms described herein may be administered as a sole therapy or in combination with another therapy or therapies.

By way of example only, if one of the side effects experienced by a patient upon receiving a compound or compound form as described herein is hypertension, then it may be appropriate to administer an anti-hypertensive agent in combination with the compound. Or, by way of example only, the therapeutic effectiveness of a compound or compound form as described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering a compound or compound form as described herein with another therapeutic agent (which also includes a therapeutic regimen) that also has therapeutic benefit. Regardless of the disease, disorder or condition being treated, the overall benefit experienced by the patient may simply be additive of the two therapeutic agents or the patient may experience a synergistic benefit.

In the instances where the compounds or compound forms as described herein are administered with other therapeutic agents, they need not be administered in the same pharmaceutical composition as other therapeutic agents, and may, because of different physical and chemical characteristics, be administered by a different route. For example, the compound or compound form as described herein may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made, e.g., according to established protocols known in the art, and then, based upon the observed effects, the dosage, modes of administration and times of administration can be modified by the skilled clinician.

The compounds, compound forms and compositions described herein (and where appropriate other chemotherapeutic agent) may be administered concurrently (e.g., simultaneously, essentially simultaneously or within the same treatment protocol) sequentially or separately, depending upon the nature of the disease, the condition of the patient, and the actual choice of other chemotherapeutic agent to be administered. For combinational applications and uses, the compounds, compound forms and compositions described herein and the chemotherapeutic agent need not be administered simultaneously or essentially simultaneously. Thus, the compounds, compound forms and compositions as described herein may be administered first followed by the administration of the chemotherapeutic agent; or the chemotherapeutic agent may be administered first followed by the administration of the compounds, compound forms and compositions as described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent may be administered first, especially if it is a cytotoxic agent, and then the treatment continued with the administration of the compounds, compound forms and compositions as described herein followed, where determined advantageous, by the administration of the chemotherapeutic agent, and so on until the treatment protocol is complete. Thus, in accordance with experience and knowledge, the practicing physician can modify each administration protocol for treatment according to the individual patient's needs, as the treatment proceeds. The attending clinician, in judging whether treatment is effective at the dosage administered, will consider the general well-being of the patient as well as more definite signs such as relief of disease-related symptoms. Relief of disease-related symptoms such as pain, and improvement in overall condition can also be used to help judge effectiveness of treatment.

Specific, non-limiting examples of possible combination therapies include use of the compounds and compositions described herein with Febuxostat, Allopurinol, Probenacid, Sulfinpyrazone, Losartan, Fenofibrate, Benzbromarone or PNP-inhibitors (such as, but not limited to Forodesine, BCX-1777 or BCX-4208). This list should not be construed to be closed, but should instead serve as an illustrative example common to the relevant therapeutic area at present. Moreover, combination regimens may include a variety of routes of administration, including but not limited to oral, intravenous, intraocular, subcutaneous, dermal, and inhaled topical.

Diseases

Described herein are methods of treating a disease or disorder in an individual suffering from said disease or disorder comprising administering to said individual an effective amount of a polymorph, crystalline form or mesophase as described herein of sodium 2-(5-bromo-4-(4-cyclopropylnaphthalen-1-yl)-4H-1,2,4-triazol-3-ylthio)acetate.

The invention extends to the use of the compounds and compound forms described herein in the manufacture of a medicament for treating a disease or disorder.

In some embodiments, the disease or disorder is hyperuricemia. In certain instances, hyperuricemia is characterized by higher than normal blood levels of uric acid, sustained over long periods of time. In certain instances, increased blood urate levels may be due to enhanced uric acid production (~10-20%) and/or reduced renal excretion (~80-90%) of uric acid. In certain instances, causes of hyperuricemia may include obesity/weight gain, excessive alcohol use, excessive dietary purine intake (foods such as shellfish, fish roe, scallops, peas lentils, beans and red meat, particularly offal—brains, kidneys, tripe, liver), certain medications, including low-dose aspirin, diuretics, niacin, cyclosporine, pyrazinamide, ethambutol, some high blood pressure drugs and some cancer chemotherapeutics, immunosuppressive and cytotoxic agents, specific disease states, particularly those associated with a high cell turnover rate (such as malignancy, leukemia, lymphoma or psoriasis), and also including high blood pressure, hemoglobin diseases, hemolytic anemia, sickle cell anemia, various nephropathies, myeloproliferative and lymphoproliferative diseases, hyperparathyroidism, renal disease, conditions associated with insulin resistance and diabetes mellitus, and in transplant recipients, and possibly heart disease, inherited enzyme defects, abnormal kidney function (e.g. increased ATP turn over, reduced glomerular urate filtration) and exposure to lead (plumbism or "saturnine gout").

In certain instances, hyperuricemia may be asymptomatic, though is associated with the following conditions: gout, gouty arthritis, uric acid stones in the urinary tract (urolithiasis), deposits of uric acid in the soft tissue (tophi), deposits of uric acid in the kidneys (uric acid nephropathy), and impaired kidney function, possibly leading to chronic and acute renal failure.

In further or additional embodiments, the disease or disorder is gout, which is a condition that results from uric acid crystals depositing in tissues of the body. It is often related to an inherited abnormality in the body's ability to process uric acid, but may also be exacerbated by a diet high in purines. Defective uric acid processing may lead to elevated levels of uric acid in the blood causing recurring attacks of joint inflammation (arthritis), uric acid deposits in and around the joints, tophaceous gout, the formation of tophi, decreased kidney function, and kidney stones. Approximately 3-5 million people in the United States suffer from attacks of gout with attacks 6 to 9 times more common in men than in women (see Sanders and Wortmann, "Harrison's Principles of Internal Medicine", 16th Edition; 2005; Food and Drug Administration (FDA) Advisory Committee Meeting, Terkeltaub presentation, June 2004; Terkeltaub, "Gout", *N Engl J Med.*, 349, 1647-55, 2003). In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Gout is associated with hyperuricemia. In certain instances, individuals suffering from gout excrete approximately 40% less uric acid than nongouty individuals for any given plasma urate concentration. In certain instances, urate levels increase until the saturation point is reached. In certain instances, precipitation of urate crystals occurs when the saturation point is reached. In certain instances, these hardened, crystallized deposits (tophi) form in the joints and skin, causing joint inflammation (arthritis). In certain instances, deposits are be made in the joint fluid (synovial fluid) and/or joint lining (synovial lining). Common areas for these deposits are the large toe, feet, ankles and hands (less common areas include the ears and eyes). In certain instances, the skin around an affected joint becomes red and shiny with the affected area being tender and painful to touch. In certain instances, gout attacks increase in frequency. In certain instances, untreated acute gout attacks lead to permanent joint damage and disability. In certain instances, tissue deposition of urate leads to: acute inflammatory arthritis, chronic arthritis, deposition of urate crystals in renal parenchyma and urolithiasis. In certain instances, the incidence of gouty arthritis increases 5 fold in individuals with serum urate levels of 7 to 8.9 mg/dL and up to 50 fold in individuals with levels >9 mg/dL (530 µmol/L). In certain instances, individuals with gout develop renal insufficiency and end stage renal disease (i.e., "gouty nephropathy"). In certain instances, gouty nephropathy is characterized by a chronic interstitial nephropathy, which is promoted by medullary deposition of monosodium urate.

In certain instances, gout includes painful attacks of acute, monarticular, inflammatory arthritis, deposition of urate crystals in joints, deposition of urate crystals in renal parenchyma, urolithiasis (formation of calculus in the urinary tract), and nephrolithiasis (formation of kidney stones). In certain instances, secondary gout occurs in individuals with cancer, particularly leukemia, and those with other blood diseases (e.g. polycythemia, myeloid metaplasia, etc).

In certain instances, attacks of gout develop very quickly, frequently the first attack occurring at night. In certain instances, symptoms include sudden, severe joint pain and extreme tenderness in the joint area, joint swelling and shiny red or purple skin around the joint. In certain instances, the attacks are infrequent lasting 5-10 days, with no symptoms between episodes. In certain instances, attacks become more frequent and last longer, especially if the disease is not controlled. In certain instances, episodes damage the affected joint(s) resulting in stiffness, swelling, limited motion and/or persistent mild to moderate pain.

Plumbism or "saturnine gout," is a lead-induced hyperuricemia that results from lead inhibition of tubular urate transport causing decreased renal excretion of uric acid. In certain instances, more than 50% of individuals suffering from lead nephropathy suffer from gout. In certain instances, acute attacks of saturnine gout occur in the knee more frequently than the big toe. In certain instances, renal disease is more frequent and more severe in saturnine gout than in primary gout. In certain instances, treatment consists of excluding the individual from further exposure to lead, the use of chelating agents to remove lead, and control of acute gouty arthritis and hyperuricaemia. In certain instances, saturnine gout is characterized by less frequent attacks than primary gout. In certain instances, lead-associated gout occurs in pre-menopausal women, an uncommon occurrence in non lead-associated gout.

In certain instances, Lesch-Nyhan syndrome (LNS or Nyhan's syndrome) affects about one in 100,000 live births. In certain instances, LNS is caused by a genetic deficiency of the enzyme hypoxanthine-guanine phosphoribosyltransferase (HGPRT). In certain instances, LNS is an X-linked recessive disease. In certain instances, LNS is present at birth in baby boys. In certain instances, the disease leads to severe gout, poor muscle control, and moderate mental retardation, which appear in the first year of life. In certain instances, the disease also results in self-mutilating behaviors (e.g., lip and finger biting, head banging) beginning in the second year of life. In certain instances, the disease also results in gout-like swelling in the joints and severe kidney problems. In certain instances, the disease leads neurological symptoms include facial grimacing, involuntary writhing, and repetitive movements of the arms and legs similar to those seen in Huntington's disease. The prognosis for individuals with LNS is poor. In certain instances, the life expectancy of an untreated individual with LNS is less than about 5 years. In certain instances, the life expectancy of a treated individual with LNS is greater than about 40 years of age.

In certain instances, hyperuricemia is found in individuals with cardiovascular disease (CVD) and/or renal disease. In certain instances, hyperuricemia is found in individuals with prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels. In certain instances, hyperuricemia is found in individuals with obesity (e.g., central obesity), high blood pressure, hyperlipidemia, and/or impaired fasting glucose. In certain instances, hyperuricemia is found in individuals with metabolic syndrome. In certain instances, gouty arthritis is indicative of an increased risk of acute myocardial infarction. In some embodiments, administration of a compound described herein to an individual are useful for decreasing the likelihood of a clinical event associated with a disease or condition linked to hyperuricemia, including, but not limited to, prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels.

In some embodiments, a compound or compound form as described herein is administered to an individual suffering from a disease or condition requiring treatment with a diuretic. In some embodiments, a compound or compound form as described herein is administered to an individual suffering from a disease or condition requiring treatment with a diuretic, wherein the diuretic causes renal retention of urate. In some embodiments, the disease or condition is congestive heart failure or essential hypertension.

In some embodiments, administration of a compound or compound form as described herein to an individual is useful for improving motility or improving quality of life.

In some embodiments, administration of a compound or compound form as described herein to an individual is useful for treating or decreasing the side effects of cancer treatment.

In some embodiments, administration of a compound or compound form as described herein to an individual is useful for decreasing kidney toxicity of cis-platin.

In certain instances, gout is treated by lowering the production of uric acid. In certain instances, gout is treated by increasing the excretion of uric acid. In certain instances, gout is treated by URAT 1, xanthine oxidase, xanthine dehydrogenase, xanthine oxidoreductase, a purine nucleoside phosphorylase (PNP) inhibitor, a uric acid transporter (URAT) inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In general, the goals of gout treatment are to i)

reduce the pain, swelling and duration of an acute attack, and ii) prevent future attacks and joint damage. In certain instances, gout attacks are treated successfully using a combination of treatments. In certain instances, gout is one of the most treatable forms of arthritis.

i) Treating the Gout Attack.

In certain instances, the pain and swelling associated with an acute attack of gout can be addressed with medications such as acetaminophen, steroids, nonsteroidal anti-inflammatory drugs (NSAIDs), adrenocorticotropic hormone (ACTH) or colchicine. In certain instances, proper medication controls gout within 12 to 24 hours and treatment is stopped after a few days. In certain instances, medication is used in conjunction with rest, increased fluid intake, ice-packs, elevation and/or protection of the affected area/s. In certain instances, the aforementioned treatments do not prevent recurrent attacks and they do not affect the underlying diseases of abnormal uric acid metabolism.

ii) Preventing Future Attacks.

In certain instances, reducing serum uric acid levels below the saturation level is the goal for preventing further gout attacks. In some cases, this is achieved by decreasing uric acid production (e.g. allopurinol), or increasing uric acid excretion with uricosuric agents (e.g. probenecid, sulfinpyrazone, benzbromarone).

In certain instances, allopurinol inhibits uric acid formation, resulting in a reduction in both the serum and urinary uric acid levels and becomes fully effective after 2 to 3 months.

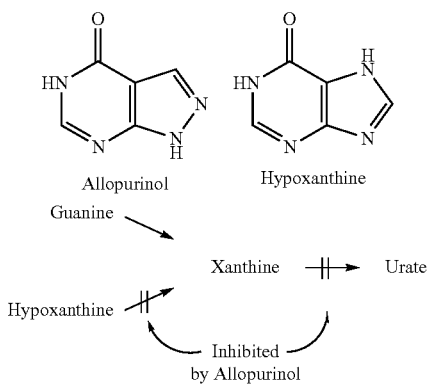

In certain instances, allopurinol is a structural analogue of hypoxanthine, (differing only in the transposition of the carbon and nitrogen atoms at positions 7 and 8), which inhibits the action of xanthine oxidase, the enzyme responsible for the conversion of hypoxanthine to xanthine, and xanthine to uric acid. In certain instances, it is metabolized to the corresponding xanthine analogue, alloxanthine (oxypurinol), which is also an inhibitor of xanthine oxidase. In certain instances, alloxanthine, though more potent in inhibiting xanthine oxidase, is less pharmaceutically acceptable due to low oral bioavailability. In certain instances, fatal reactions due to hypersensitivity, bone marrow suppression, hepatitis, and vasculitis have been reported with Allopurinol. In certain instances, the incidence of side effects may total 20% of all individuals treated with the drug. Treatment for diseases of uric acid metabolism has not evolved significantly in the following two decades since the introduction of allopurinol.

In certain instances, uricosuric agents (e.g., probenecid, sulfinpyrazone, and benzbromarone) increase uric acid excretion. In certain instances, probenecid causes an increase in uric acid secretion by the renal tubules and, when used chronically, mobilizes body stores of urate. In certain instances, 25-50% of individuals treated with probenecid fail to achieve reduction of serum uric acid levels <6 mg/dL. In certain instances, insensitivity to probenecid results from drug intolerance, concomitant salicylate ingestion, and renal impairment. In certain instances, one-third of the individuals develop intolerance to probenecid. In certain instances, administration of uricosuric agents also results in urinary calculus, gastrointestinal obstruction, jaundice and anemia.

Successful treatment aims to reduce both the pain associated with acute gout flare and long-term damage to the affected joints (Emerson, "The Management of Gout", N Engl J Med., 334(7), 445-451, 1996). Therapeutic goals include providing rapid and safe pain relief, preventing further attacks, preventing the formation of tophi and subsequent arthritis, and avoiding exacerbating other medical conditions. Initiation of treatment depends upon the underlying causes of hyperuricemia, such as renal function, diet, and medications. While gout is a treatable condition, there are limited treatments available for managing acute and chronic gout and a number of adverse effects are associated with current therapies. Medication treatment of gout includes pain management, prevention or decrease in joint inflammation during an acute gouty attack, and chronic long-term therapy to maintain decreased serum uric acid levels.

Nonsteroidal anti-inflammatory drugs (NSAIDs) are effective anti-inflammatory medications for acute gout but are frequently associated with irritation of the gastrointestinal (GI) system, ulceration of the stomach and intestines, and occasionally intestinal bleeding (Schlesinger, "Management of Acute and Chronic Gouty Arthritis Present State-of-the-Art"; Medications; 64 (21), 2399-2416, 2004; Pascual and Sivera, "Therapeutic advances in gout"; Curr Opin Rheumatol., March; 19(2), 122-7, 2007). Colchicine for acute gout is most commonly administered orally as tablets (every 1-2 hours until there is significant improvement in pain or the patient develops GI side effects such as severe diarrhea, nausea and vomiting), or intravenously. Corticosteroids, given in short courses, can be administered orally or injected directly into the inflamed joint.

Medications are available for reducing blood uric acid levels that either increase renal excretion of uric acid by inhibiting re-uptake or reduce production of uric acid by blockade of xanthine oxidase. These medicines are generally not initiated until after the inflammation from acute gouty arthritis has subsided because they may intensify the attack. If they are already being taken prior to the attack, they are continued and only adjusted after the attack has resolved. Since many subjects with elevated blood uric acid levels may not develop gouty attacks or kidney stones, the decision for prolonged treatment with uric acid-lowering medications is individualized.

Kits

The compounds, compound forms, compositions and methods described herein provide kits for the treatment of diseases and disorders, such as the ones described herein. These kits comprise a compound, compound form, compounds, compound forms or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

Provided in certain embodiments, are compositions or kits comprising sodium 2-(5-bromo-4-(4-cyclopropylnaphthalen-1-yl)-4H-1,2,4-triazol-3-ylthio)acetate (e.g., a polymorph thereof, such as Form A), a double low density polyethylene plastic bag, and an HDPE container. In further embodiments, the composition or kit further comprises a foil bag (e.g., an anhydrous foil bag, such as a heat sealed anhydrous foil bag). In some embodiments, the composition or kit further comprises a desiccant; in still other embodiments, a desiccant is not necessary and/or present. In some instances, such packing improves the stability of the sodium 2-(5-bromo-4-(4-cyclopropylnaphthalen-1-yl)-4H-1,2,4-triazol-3-ylthio)acetate (e.g., Form A).

The compounds, compound forms and pharmaceutical compositions described herein may be utilized for diagnostics and as research reagents. For example, the compounds, compound forms and pharmaceutical compositions, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds, compound forms and pharmaceutical compositions described herein are also useful for veterinary treatment of companion animals (e.g. dogs, cats), exotic animals and farm animals (e.g. horses), including mammals, rodents, and the like.

The examples and preparations provided below further illustrate and exemplify the compounds of the present invention and methods of preparing such compounds. It is to be understood that the scope of the present invention is not limited in any way by the scope of the following examples and preparations.

EXAMPLES

I Preparation of Compounds

Example 1

Preparation of sodium 2-(5-bromo-4-(4-cyclopropylnaphthalen-1-yl)-4H-1,2,4-triazol-3-ylthio)acetate Sodium 2-(5-bromo-4-(4-cyclopropylnaphthalen-1-yl)-4H-1,2,4-triazol-3-ylthio)acetate was prepared according to previously described procedures (see US patent publication 2009/0197825) and as outlined below.

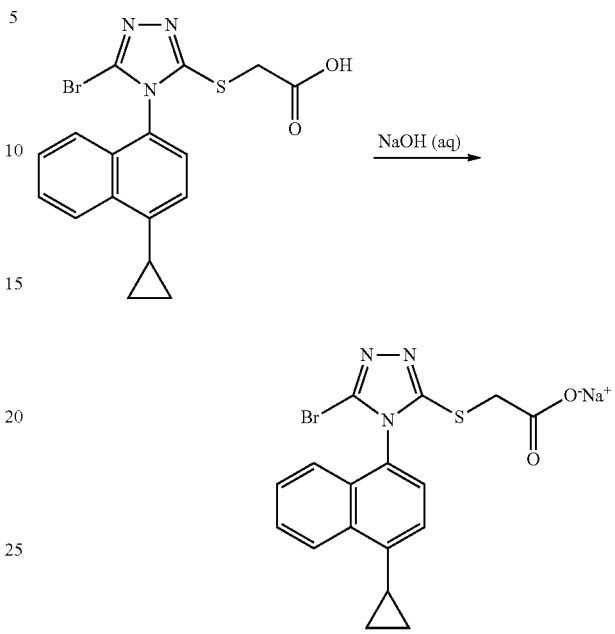

Aqueous sodium hydroxide solution (1M, 2.0 mL, 2.0 mmol) was added dropwise over 5 min to a solution of 2-(5-bromo-4-(1-cyclopropylnaphthalen-4-yl)-4H-1,2,4-triazol-3-ylthio)acetic acid (810 mg, 2.0 mmol) in ethanol (10 mL) at 10° C. The mixture was stirred at 10° C. for a further 10 min. Volatile solvents were removed in vacuo to dryness to provide sodium 2-(5-bromo-4-(4-cyclopropylnaphthalen-1-yl)-4H-1,2,4-triazol-3-ylthio)acetate as a solid (850 mg, 100%).

Example 2

Preparation of 2-(5-Bromo-4-(4-cyclopropylnaphthalen-1-yl)-4H-1,2,4-triazol-3-ylthio)acetic acid 2-(5-Bromo-4-(4-cyclopropylnaphthalen-1-yl)-4H-1,2,4-triazol-3-ylthio)acetic acid was prepared according to previously described procedures (see US patent publication 2009/0197825) and as outlined below.

Route i:

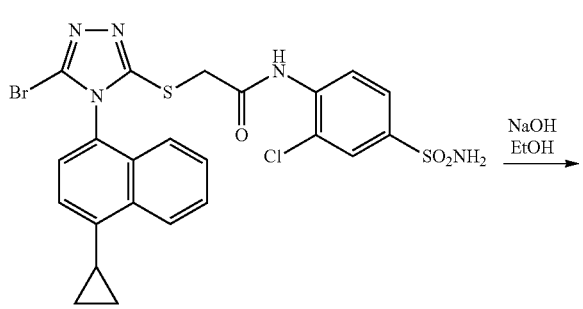

-continued

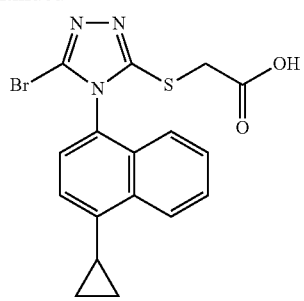

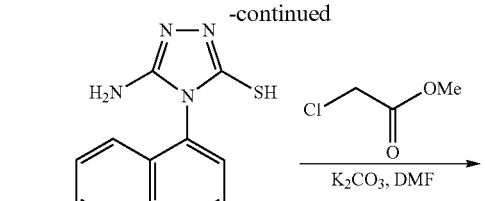

Sodium hydroxide solution (2M aqueous, 33.7 mL, 67 mmol, 2 eq) was added to a suspension of 2-(5-bromo-4-(4-cyclopropylnaphthalen-1-yl)-4H-1,2,4-triazol-3-ylthio)-N-(2-chloro-4-sulfamoylphenyl)acetamide (prepared by previously published procedures, see US 2009/0197825; 20 g, 34 mmol) in ethanol (200 mL) and the mixture heated at reflux for 4 hours. Charcoal (10 g) was added, the mixture stirred at room temperature for 12 hours and the charcoal removed by filtration. The charcoal was washed several times with ethanol and the filtrate then concentrated. Water (200 mL) was added and then concentrated to approx. one third volume to remove all ethanol. Water (200 mL) and ethyl acetate (250 mL) were added, the mixture stirred vigorously for 15 min and the organic layer removed. The aqueous layer was cooled to 0° C. and acidified by treatment with HCl (1N) resulting in the formation of a cloudy oily precipitate. The mixture was extracted with ethyl acetate (3×) and the combined organic extracts dried over sodium sulfate and concentrated to give 2-(5-bromo-4-(4-cyclopropylnaphthalen-1-yl)-4H-1,2,4-triazol-3-ylthio)acetic acid as an off white solid (11.2 g, 82%).

Route ii:

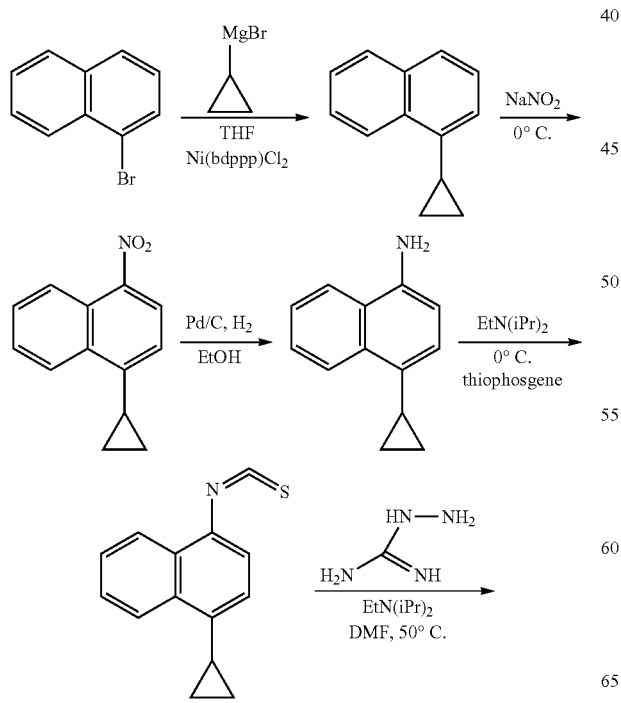

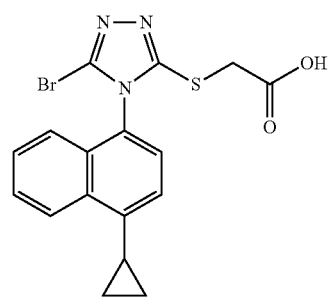 [SMILES: O=C(O)CSc1nnc(Br)n1-c1ccc(C2CC2)c2ccccc12]

STEP A: 1-Cyclopropylnaphthalene

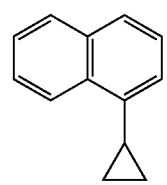 [SMILES: c1ccc2c(C3CC3)cccc2c1]

Cyclopropylmagnesium bromide (150 mL, 0.5M in tetrahydrofuran) was slowly added to a solution of 1-bromonaphthalene (10 g, 50 mmol) and [1,3-bis(diphenylphosphino)propane]dichloro nickel (II) in tetrahydrofuran (10 mL) stirred at 0° C., and the reaction mixture stirred at room temperature for 16 hours. The solvent was removed under reduced pressure and ethyl acetate and aqueous ammonium chloride were added. After extraction, the organic layer was dried over sodium sulfate, filtered and concentrated under reduced pressure. The residue was purified by silica gel chromatography to yield 1-cyclopropylnaphthalene (6.4 g, 76%).

STEP B: 1-Cyclopropyl-4-nitronaphthalene

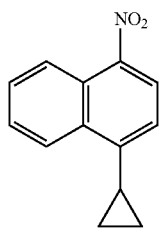 [SMILES: O=[N+]([O-])c1ccc(C2CC2)c2ccccc12]

Sodium nitrite (30 mL) was slowly added (over 2 hours) to 1-cyclopropylnaphthalene (6.4 g, 38 mmol) stirred at 0° C. The reaction mixture was stirred at 0° C. for an extra 30 min and then slowly poured into ice. Water was added, followed by ethyl acetate. After extraction, the organic layer was washed with aqueous sodium hydroxide (1%) and water, dried over sodium sulfate, filtered and concentrated under reduced pressure. The residue was purified by silica gel chromatography to yield 1-cyclopropyl-4-nitronaphthalene (5.2 g, 64%).

STEP C: 1-Amino-4-cyclopropylnaphthalene

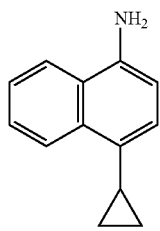 [SMILES: Nc1ccc(C2CC2)c2ccccc12]

A solution of 1-cyclopropyl-4-nitronaphthalene (5 g, 23 mmol) in ethanol (200 mL) was stirred under hydrogen in the presence of Pd/C (10% net, 1.8 g). The reaction mixture was shaken overnight, filtered over celite, and concentrated under reduced pressure. The residue was purified by silica gel chromatography to yield 1-amino-4-cyclopropylnaphthalene (3.1 g, 73%).

STEP D: 1-Cyclopropyl-4-isothiocyanatonaphthalene

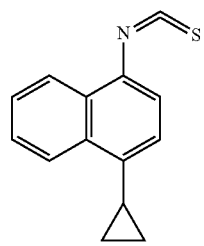 [SMILES: S=C=Nc1ccc(C2CC2)c2ccccc12]

Thiophosgene (1.1 g, 9.7 mmol) was added to a stirred solution of 1-amino-4-cyclopropylnaphthalene (1.8 g, 9.7 mmol) and diisopropylethylamine (2 eq) in dichloromethane (50 mL) at 0° C. The reaction mixture was stirred for 5 min at 0° C. and then aqueous HCl (1% solution) was added. The organic layer was separated, washed with brine, dried over sodium sulfate, filtered and the solvent removed under reduced pressure. Hexane was added, and the resulting precipitate was filtered. The solvent was evaporated to yield 1-cyclopropyl-4-isothiocyanatonaphthalene (1.88 g, 86%).

STEP E: 5-Amino-4-(1-cyclopropylnaphthalen-4-yl)-4H-1,2,4-triazole-3-thiol

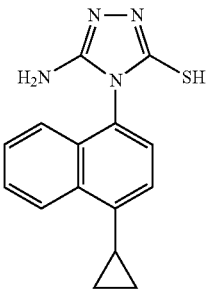 [SMILES: Nc1nnc(S)n1-c1ccc(C2CC2)c2ccccc12]

A mixture of aminoguanidine hydrochloride (3.18 g, 29 mmol), 1-cyclopropyl-4-isothiocyanato naphthalene (3.24 g, 14 mmol) and diisopropylethylamine (3 eq) in DMF (20 mL) was stirred at 50° C. for 15 hours. The solvent was removed under reduced pressure, toluene added, and the solvent was evaporated again. Sodium hydroxide solution (2M, 30 mL) was added and the reaction mixture heated at 50° C. for 60 hours. The reaction mixture was filtered and the filtrate neutralized with aqueous HCl (2M). The mixture was re-filtered and the solvent removed under reduced pressure. The residue was purified by silica gel chromatography to yield 5-amino-4-(1-cyclopropylnaphthalen-4-yl)-4H-1,2,4-triazole-3-thiol (2.0 g, 49%).

STEP F: Methyl 2-(5-amino-4-(1-cyclopropylnaphthalen-4-yl)-4H-1,2,4-triazol-3-ylthio)acetate

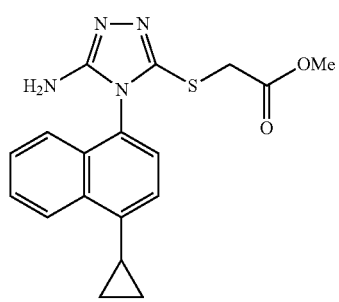 [SMILES: COC(=O)CSc1nnc(N)n1-c1ccc(C2CC2)c2ccccc12]

Methyl 2-chloroacetate (0.73 mL, 8.3 mmol) was added dropwise over 5 min to a suspension of 5-amino-4-(1-cyclopropylnaphthalen-4-yl)-4H-1,2,4-triazole-3-thiol (2.24 g, 7.9 mmol) and potassium carbonate (1.21 g, 8.7 mmol) in DMF (40 mL) at room temperature. The reaction was stirred at room temperature for 24 h and slowly poured into a stirred ice-cold water solution. The tan precipitate was collected by vacuum filtration and dried under high vacuum at 50° C. for 16 h in the presence of P₂O₅ to yield methyl 2-(5-amino-4-(1-cyclopropylnaphthalen-4-yl)-4H-1,2,4-triazol-3-ylthio)acetate (2.24 g, 80%).

STEP G: Methyl 2-(5-bromo-4-(1-cyclopropylnaphthalen-4-yl)-4H-1,2,4-triazol-3-ylthio)acetate

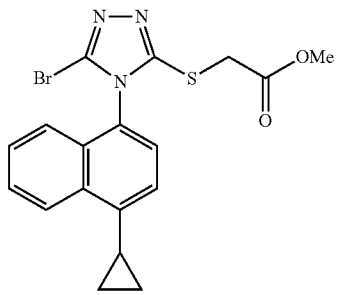 [SMILES: COC(=O)CSc1nnc(Br)n1-c1ccc(C2CC2)c2ccccc12]

Sodium nitrite (2.76 g, 40 mmol) was added to a solution of methyl 2-(5-amino-4-(1-cyclopropylnaphthalen-4-yl)-4H-1,2,4-triazol-3-ylthio)acetate (0.71 g, 2 mmol) and benzyltriethylammonium chloride (1.63 g, 6 mmol) in bromoform (10 mL). Dichloroacetic acid (0.33 mL, 4 mmol) was then added and the reaction mixture stirred at room temperature for 3 h. The mixture was directly loaded onto a 7-inch column of silica gel, packed with dichloromethane (DCM). The column was first eluted with DCM until all bromoform eluted, then eluted with acetone/DCM (5:95) to give methyl 2-(5-bromo-4-(1-cyclopropylnaphthalen-4-yl)-4H-1,2,4-triazol-3-ylthio)acetate (713 mg, 85%).

STEP H: 2-(5-Bromo-4-(1-cyclopropylnaphthalen-4-yl)-4H-1,2,4-triazol-3-ylthio)acetic acid

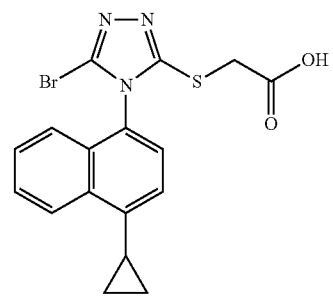 [SMILES: O=C(O)CSc1nnc(Br)n1-c1ccc(C2CC2)c2ccccc12]

A solution of lithium hydroxide (98 mg, 4.1 mmol) in water (10 mL) was added dropwise over 5 min to a solution of methyl 2-(5-bromo-4-(1-cyclopropylnaphthalen-4-yl)-4H-1,2,4-triazol-3-ylthio)acetate (1.14 g, 2.7 mmol) in ethanol (10 mL) and THF (10 mL) at 0° C.

The mixture was stirred at 0° C. for a further 45 min and then neutralized to pH 7 by the addition of 0.5N HCl solution at 0° C. The resulting mixture was concentrated in vacuo to ⅕th of its original volume, then diluted with water (~20 mL) and acidified to pH 2-3 by the addition of 0.5N HCl to produce a sticky solid. (If the product comes out as an oil during acidification, extraction with dichloromethane is recommended.) The tan solid was collected by vacuum filtration and dried under high vacuum at 50° C. for 16 h in the presence of P₂O₅ to yield 2-(5-bromo-4-(1-cyclopropylnaphthalen-4-yl)-4H-1,2,4-triazol-3-ylthio)acetic acid (1.02 g, 93%).

II Preparation and Analysis of Various Polymorphic, Crystalline and Mesophase Forms General Solvent Techniques Solvents:

Solvents were either HPLC grade or ACS grade.

Evaporation:

Solvents were added to weighed solids and heated, agitated and/or sonicated to facilitate dissolution as required. The resulting solutions were filtered into clean containers and left uncovered (fast evaporation) or with a loose cap (slow evaporation) in a laboratory fume hood under ambient conditions or on a stir plate at ambient, elevated or sub-ambient temperatures. Samples were evaporated until no solvent was visible, generally to dryness.

Slurry:

Slurries were prepared by adding enough solids to a given solvent or solvent mixture so that excess solids were present. The mixture was then stirred in a sealed vial (unless it was evaporation slurry) at ambient, elevated, or sub-ambient temperatures. The solids were isolated by vacuum or positive pressure filtration or solvent decantation. Low solubility solvents slurries were spiked with a small volume of high solubility solvent to encourage conversion. Elevated temperature slurries seeking increased solid yield and/or crystallization initiation were slow cooled by shutting off the heat.

Trituration:

Samples that generated oil and/or gel were scratched/scraped with a dental pick or spatula to encourage crystallization.

Polymorphic Forms A, B and B'

Three polymorphic forms of sodium 2-(5-bromo-4-(4-cyclopropylnaphthalen-1-yl)-4H-1,2,4-triazol-3-ylthio)acetate were prepared.

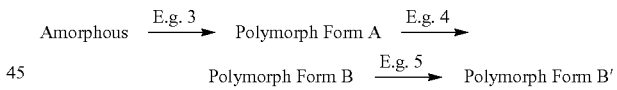

Example 3A

Preparation of Crystalline Polymorph Form A of Sodium 2-(5-bromo-4-(4-cyclopropylnaphthalen-1-yl)-4H-1,2,4-triazol-3-ylthio)acetate Deionized water (0.5 mL) was added to a stirred suspension of amorphous sodium 2-(5-bromo-4-(4-cyclopropylnaphthalen-1-yl)-4H-1,2,4-triazol-3-ylthio)acetate (1.00 g containing 1.8 wt % water) and ethyl acetate (4 mL) producing a bi-phasic mixture, which was stirred at room temperature for 18 hours. The resulting slurry was filtered under vacuum and the solids washed with ethyl acetate (2×10 mL). The filter cake was dried in vacuo at 18-20° C. with a nitrogen sweep for 4.5 hours to give 0.78 g sodium 2-(5-bromo-4-(4-cyclopropylnaphthalen-1-yl)-4H-1,2,4-triazol-3-ylthio)acetate containing 13.0 wt % water (70.3% recovery, anhydrous basis). The isolated solid was designated Form A.

Example 3B

Analysis of Crystalline Polymorph Form A of Sodium 2-(5-bromo-4-(4-cyclopropylnaphthalen-1-yl)-4H-1,2,4-triazol-3-ylthio)acetate X-ray powder Diffraction One Panalytical and one Inel XRPD pattern were analyzed. The reproducibility and relative peak intensities were in good agreement between the x-ray powder diffraction patterns, indicating good particle and orientation statistics. The XRPD pattern for Form A is shown in FIG. 1; observed and representative peaks in the XRPD pattern are shown in the tables below:

| Form A Observed | | |
|---|---|---|
| °2θ | d space (Å) | Intensity (%) |
| 4.90 ± 0.10 | 18.027 ± 0.375 | 71 |
| 6.86 ± 0.10 | 12.891 ± 0.191 | 100 |
| 8.41 ± 0.10 | 10.512 ± 0.126 | 61 |
| 9.83 ± 0.10 | 8.996 ± 0.092 | 63 |
| 10.13 ± 0.10 | 8.730 ± 0.087 | 97 |
| 10.60 ± 0.10 | 8.346 ± 0.079 | 16 |
| 11.92 ± 0.10 | 7.424 ± 0.063 | 45 |
| 12.32 ± 0.10 | 7.183 ± 0.059 | 45 |
| 12.57 ± 0.10 | 7.041 ± 0.056 | 45 |
| 13.07 ± 0.10 | 6.772 ± 0.052 | 42 |
| 14.01 ± 0.10 | 6.322 ± 0.045 | 21 |
| 14.48 ± 0.10 | 6.118 ± 0.042 | 35 |
| 14.80 ± 0.10 | 5.988 ± 0.041 | 23 |
| 15.15 ± 0.10 | 5.850 ± 0.039 | 52 |
| 16.28 ± 0.10 | 5.444 ± 0.033 | 18 |
| 16.70 ± 0.10 | 5.309 ± 0.032 | 20 |
| 16.90 ± 0.10 | 5.246 ± 0.031 | 22 |
| 17.92 ± 0.10 | 4.950 ± 0.028 | 70 |
| 18.64 ± 0.10 | 4.761 ± 0.025 | 36 |
| 20.88 ± 0.10 | 4.255 ± 0.020 | 42 |
| 21.35 ± 0.10 | 4.163 ± 0.019 | 25 |
| 21.68 ± 0.10 | 4.099 ± 0.019 | 18 |
| 22.42 ± 0.10 | 3.966 ± 0.018 | 38 |
| 23.10 ± 0.10 | 3.850 ± 0.017 | 55 |
| 23.54 ± 0.10 | 3.780 ± 0.016 | 20 |
| 23.95 ± 0.10 | 3.715 ± 0.015 | 37 |
| 24.67 ± 0.10 | 3.609 ± 0.014 | 44 |
| 25.29 ± 0.10 | 3.522 ± 0.014 | 68 |
| 26.38 ± 0.10 | 3.379 ± 0.013 | 33 |
| 26.96 ± 0.10 | 3.307 ± 0.012 | 33 |
| 27.63 ± 0.10 | 3.229 ± 0.012 | 22 |
| 28.36 ± 0.10 | 3.147 ± 0.011 | 29 |
| 29.07 ± 0.10 | 3.072 ± 0.010 | 35 |

| Form A Representative | | |
|---|---|---|
| °2θ | d space (Å) | Intensity (%) |
| 4.90 ± 0.10 | 18.027 ± 0.375 | 71 |
| 6.86 ± 0.10 | 12.891 ± 0.191 | 100 |
| 8.41 ± 0.10 | 10.512 ± 0.126 | 61 |
| 9.83 ± 0.10 | 8.996 ± 0.092 | 63 |
| 10.13 ± 0.10 | 8.730 ± 0.087 | 97 |
| 17.92 ± 0.10 | 4.950 ± 0.028 | 70 |
| 23.10 ± 0.10 | 3.850 ± 0.017 | 55 |
| 25.29 ± 0.10 | 3.522 ± 0.014 | 68 |

The differential scanning calorimetry trace for Form A is shown in FIG. 2.

Figure 3:
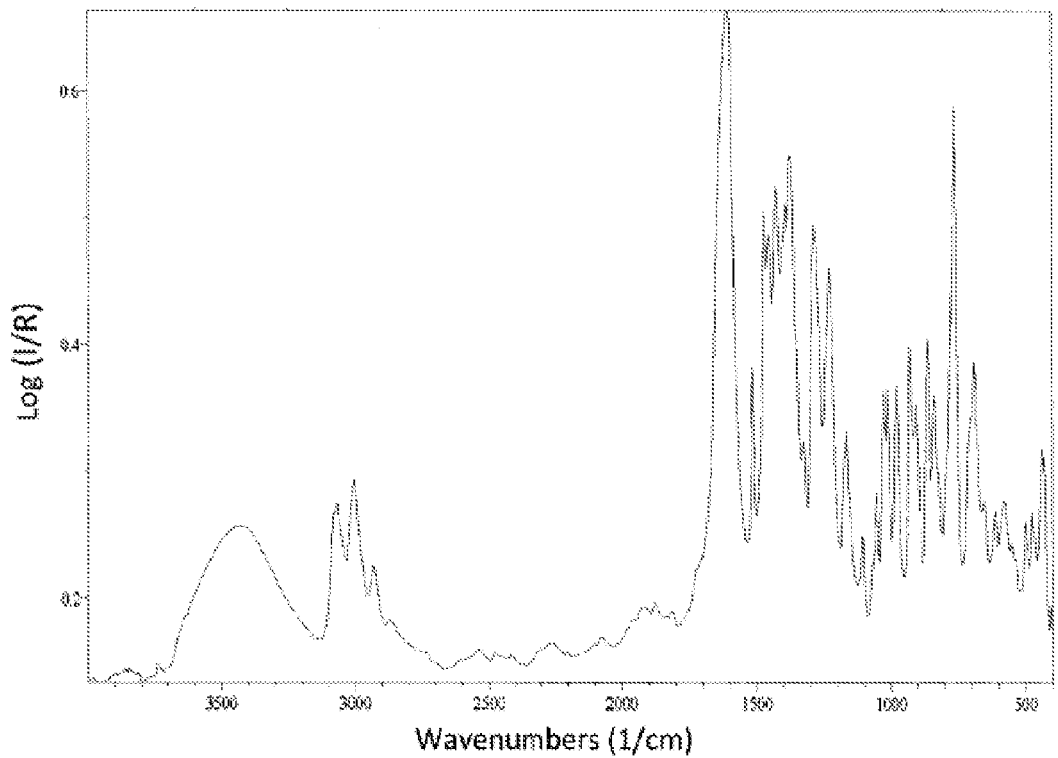
FIG. 3 represents an illustrative infrared spectrum of Polymorph Form A.

The infrared absorption spectrum of Form A is shown in FIG. 3.

Figure 4:
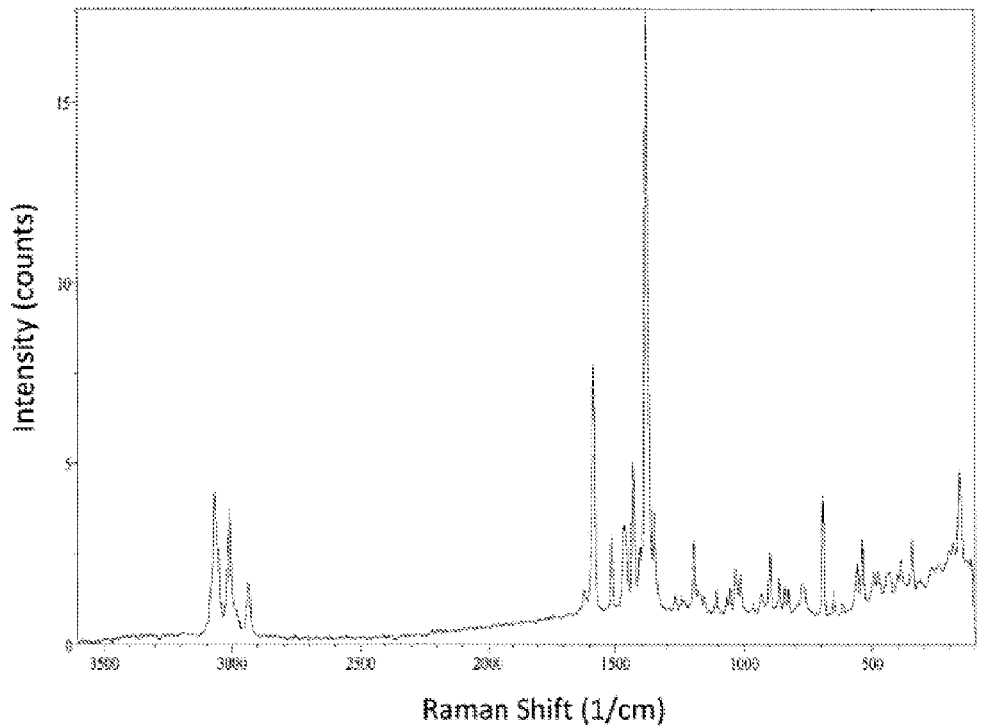
FIG. 4 represents an illustrative Raman spectrum of Polymorph Form A.

The Raman spectrum of Form A is shown in FIG. 4.

Form A of sodium 2-(5-bromo-4-(4-cyclopropylnaphthalen-1-yl)-4H-1,2,4-triazol-3-ylthio)acetate was tested under various conditions to determine thermodynamic stability. No degradation of packaged Form A was observed for 6 months under accelerated conditions (40° C.-75% RH). Moreover, no degradation of packaged Form A was observed for 12 months under long term conditions (25° C.-60% RH). Packaging was in a double low density polyethylene plastic bag inside a heat sealed anhydrous foil bag in an HDPE container. The stability results of Form A demonstrated an improvement over the solid state amorphous free acid.

Example 4A

Preparation of Crystalline Polymorph Form B of Sodium 2-(5-bromo-4-(4-cyclopropylnaphthalen-1-yl)-4H-1,2,4-triazol-3-ylthio)acetate Preparation i:

A mixture of sodium 2-(5-bromo-4-(4-cyclopropylnaphthalen-1-yl)-4H-1,2,4-triazol-3-ylthio)acetate (3.02 g, Form A) and water-saturated ethyl acetate (6 mL) was stirred at 45-50° C. for 16 hours producing a bi-phasic mixture, which was gradually cooled to room temperature over 2 hours and stirred for an additional 21 hours to give a uniform suspension. The suspension was vacuum filtered, washed with ethyl acetate and the filter cake dried in vacuo at 18-20° C. with a nitrogen sweep for 2 hours to give 2.77 g sodium 2-(5-bromo-4-(4-cyclopropylnaphthalen-1-yl)-4H-1,2,4-triazol-3-ylthio)acetate containing 12.9 wt % water (91.7% recovery, anhydrous basis).

Preparation ii:

Sodium 2-(5-bromo-4-(4-cyclopropylnaphthalen-1-yl)-4H-1,2,4-triazol-3-ylthio)acetate (Form A) was stirred at ~50° C. in water-saturated ethyl acetate (0.5 mL) overnight, converting the solids to oil. The oil was scratched with a dental pick and left to stir at ambient temperature. After ~3 days, optical microscopy indicated crystalline solids. The liquid was removed by decantation and the solids isolated. The isolated solids were designated Form B.

Example 4B

Analysis of Crystalline Polymorph Form B of Sodium 2-(5-bromo-4-(4-cyclopropylnaphthalen-1-yl)-4H-1,2,4-triazol-3-ylthio)acetate X-Ray Powder Diffraction One Panalytical and one Inel XRPD pattern were analyzed. The reproducibility and relative peak intensities were in good agreement between the x-ray powder diffraction patterns, indicating good particle and orientation statistics. The XRPD pattern for Form B is shown in FIG. 5; observed and representative peaks in the XRPD pattern are shown in the tables below:

| Form B Observed | | |
|---|---|---|
| °2θ | d space (Å) | Intensity (%) |
| 4.22 ± 0.10 | 20.939 ± 0.508 | 100 |
| 8.51 ± 0.10 | 10.392 ± 0.123 | 79 |
| 12.80 ± 0.10 | 6.917 ± 0.054 | 40 |
| 13.97 ± 0.10 | 6.337 ± 0.045 | 20 |
| 14.46 ± 0.10 | 6.126 ± 0.042 | 21 |

Form B Observed

| °2θ | d space (Å) | Intensity (%) |
|---|---|---|
| 16.19 ± 0.10 | 5.475 ± 0.034 | 23 |
| 16.95 ± 0.10 | 5.231 ± 0.031 | 45 |
| 18.40 ± 0.10 | 4.821 ± 0.026 | 22 |
| 19.13 ± 0.10 | 4.639 ± 0.024 | 26 |
| 19.48 ± 0.10 | 4.558 ± 0.023 | 24 |
| 20.03 ± 0.10 | 4.433 ± 0.022 | 25 |
| 21.28 ± 0.10 | 4.176 ± 0.019 | 23 |
| 22.56 ± 0.10 | 3.942 ± 0.017 | 32 |
| 22.90 ± 0.10 | 3.883 ± 0.017 | 27 |
| 23.53 ± 0.10 | 3.781 ± 0.016 | 24 |
| 25.64 ± 0.10 | 3.474 ± 0.013 | 28 |
| 27.27 ± 0.10 | 3.271 ± 0.012 | 18 |
| 28.17 ± 0.10 | 3.168 ± 0.011 | 15 |
| 28.72 ± 0.10 | 3.108 ± 0.011 | 19 |

Form B Representative

| °2θ | d space (Å) | Intensity (%) |
|---|---|---|
| 4.22 ± 0.10 | 20.939 ± 0.508 | 100 |
| 8.51 ± 0.10 | 10.392 ± 0.123 | 79 |
| 12.80 ± 0.10 | 6.917 ± 0.054 | 40 |
| 16.95 ± 0.10 | 5.231 ± 0.031 | 45 |

The differential scanning calorimetry trace for Form B is shown in FIG. 6.

Example 5A

Preparation of Crystalline Polymorph Form B' of Sodium 2-(5-bromo-4-(4-cyclopropylnaphthalen-1-yl)-4H-1,2,4-triazol-3-ylthio)acetate Sodium 2-(5-bromo-4-(4-cyclopropylnaphthalen-1-yl)-4H-1,2,4-triazol-3-ylthio)acetate (Form B containing 12.9 wt % water) was dried under vacuum at ambient temperature for 1-3 days resulting in an off-white solid, designated as form B'.

Example 5B

Analysis of Crystalline Polymorph Form B' of Sodium 2-(5-bromo-4-(4-cyclopropylnaphthalen-1-yl)-4H-1,2,4-triazol-3-ylthio)acetate The x-ray powder diffraction pattern for Form B', shown in FIG. 7, resembles that of Form B, however with non-uniform peak shifts between the patterns, suggesting a different solvation state of the same polymorph. The differential scanning calorimetry trace of Form B' is shown in FIG. 8.

Stability of Crystalline Polymorph Sodium 2-(5-bromo-4-(4-cyclopropylnaphthalen-1-yl)-4H-1,2,4-triazol-3-ylthio)acetate The crystalline polymorphs of sodium 2-(5-bromo-4-(4-cyclopropylnaphthalen-1-yl)-4H-1,2,4-triazol-3-ylthio)acetate were found to exhibit increased stability in comparison to the amorphous solid state form of the carboxylic acid. The improved stability of the crystalline polymorphs of sodium 2-(5-bromo-4-(4-cyclopropylnaphthalen-1-yl)-4H-1,2,4-triazol-3-ylthio)acetate provides for the preparation of pharmaceutical dosage forms displaying reduced variability in the dosage present in a given dosage form, reduction in the presence of impurities in the final pharmaceutical product, and an improved shelf life of formulated dosage forms when compared to the pharmaceutical dosage form prepared with the amorphous solid state form of the carboxylic acid.

Unique Crystalline X-Ray Powder Diffraction Patterns C, D and E

Example 6

Sodium 2-(5-bromo-4-(4-cyclopropylnaphthalen-1-yl)-4H-1,2,4-triazol-3-ylthio)acetate Generated Three Additional Unique Crystalline X-Ray Powder Diffraction Patterns—Patterns C, D and E, Prepared as Follows Pattern C: fast evaporation from methanol at ~97% relative humidity.
Pattern D: cold crystallization from ethanol/water.
Pattern E: cold crystallization from 2-propanol/water.

Example 6A

Sodium 2-(5-bromo-4-(4-cyclopropylnaphthalen-1-yl)-4H-1,2,4-triazol-3-ylthio)acetate Displaying Unique Crystalline X-Ray Powder Diffraction Pattern C A portion of Form A was dissolved in methanol, followed by fast evaporation at 97% relative humidity. One Bruker XRPD pattern was analyzed for this material, and preferred orientation and particle statistic effects assessed through evaluation of the two dimensional scattering pattern. Consistent, uninterrupted rings devoid of spots suggest good particle and orientation statistics. XRPD pattern C is shown in FIG. 9; observed and representative peaks in the XRPD pattern are shown in the table below:

| Pattern C Observed | | | Pattern C Representative | | |
|---|---|---|---|---|---|
| °2θ | d space (Å) | Intensity (%) | °2θ | d space (Å) | Intensity (%) |
| 6.9 ± 0.1 | 12.774 ± 0.187 | 100 | 6.9 ± 0.1 | 12.774 ± 0.187 | 100 |
| 7.7 ± 0.1 | 11.512 ± 0.152 | 6 | 10.1 ± 0.1 | 8.758 ± 0.087 | 88 |
| 8.2 ± 0.1 | 10.809 ± 0.134 | 6 | 22.6 ± 0.1 | 3.941 ± 0.017 | 87 |
| 8.6 ± 0.1 | 10.306 ± 0.121 | 10 | 23.3 ± 0.1 | 3.811 ± 0.016 | 74 |
| 10.1 ± 0.1 | 8.758 ± 0.087 | 88 | 23.9 ± 0.1 | 3.726 ± 0.015 | 80 |
| 11.0 ± 0.1 | 8.014 ± 0.073 | 24 | 25.2 ± 0.1 | 3.534 ± 0.014 | 84 |
| 12.5 ± 0.1 | 7.059 ± 0.057 | 32 | 28.3 ± 0.1 | 3.158 ± 0.011 | 66 |

-continued

| Pattern C Observed | | | Pattern C Representative | | |
|---|---|---|---|---|---|
| °2θ | d space (Å) | Intensity (%) | °2θ | d space (Å) | Intensity (%) |
| 13.1 ± 0.1 | 6.779 ± 0.052 | 26 | 29.0 ± 0.1 | 3.075 ± 0.010 | 70 |
| 14.0 ± 0.1 | 6.308 ± 0.045 | 14 | | | |
| 15.4 ± 0.1 | 5.746 ± 0.037 | 10 | | | |
| 16.7 ± 0.1 | 5.315 ± 0.032 | 12 | | | |
| 17.6 ± 0.1 | 5.051 ± 0.029 | 34 | | | |
| 18.4 ± 0.1 | 4.827 ± 0.026 | 23 | | | |
| 19.1 ± 0.1 | 4.656 ± 0.024 | 11 | | | |
| 19.8 ± 0.1 | 4.480 ± 0.022 | 13 | | | |
| 20.2 ± 0.1 | 4.388 ± 0.022 | 20 | | | |
| 21.1 ± 0.1 | 4.215 ± 0.020 | 19 | | | |
| 21.8 ± 0.1 | 4.081 ± 0.019 | 42 | | | |
| 22.6 ± 0.1 | 3.941 ± 0.017 | 87 | | | |
| 23.3 ± 0.1 | 3.811 ± 0.016 | 74 | | | |
| 23.9 ± 0.1 | 3.726 ± 0.015 | 80 | | | |
| 25.2 ± 0.1 | 3.534 ± 0.014 | 84 | | | |
| 26.4 ± 0.1 | 3.376 ± 0.013 | 40 | | | |
| 27.1 ± 0.1 | 3.295 ± 0.012 | 34 | | | |
| 28.3 ± 0.1 | 3.158 ± 0.011 | 66 | | | |
| 29.0 ± 0.1 | 3.075 ± 0.010 | 70 | | | |

Example 6B

Preparation of Sodium 2-(5-bromo-4-(4-cyclopropyl-naphthalen-1-yl)-4H-1,2,4-triazol-3-ylthio)acetate Displaying Unique Crystalline X-Ray Powder Diffraction Pattern D A portion of Form A was crystallized in a freezer from an ethanol/water (1/1) solution. One Bruker XRPD pattern was analyzed for this material, and preferred orientation and particle statistic effects assessed through evaluation of the two dimensional scattering pattern. Consistent, uninterrupted rings devoid of spots suggest good particle and orientation statistics. XRPD pattern D is shown in FIG. 10; observed and representative peaks in the XRPD pattern are shown in the table below:

| Pattern D Observed | | | Pattern D Representative | | |
|---|---|---|---|---|---|
| °2θ | d space (Å) | Intensity (%) | °2θ | d space (Å) | Intensity (%) |
| 6.1 ± 0.1 | 14.585 ± 0.244 | 20 | 10.3 ± 0.1 | 8.605 ± 0.084 | 100 |
| 6.5 ± 0.1 | 13.599 ± 0.212 | 10 | 17.8 ± 0.1 | 4.994 ± 0.028 | 43 |
| 6.9 ± 0.1 | 12.737 ± 0.186 | 11 | 25.2 ± 0.1 | 3.531 ± 0.014 | 66 |
| 7.3 ± 0.1 | 12.177 ± 0.170 | 31 | | | |
| 10.3 ± 0.1 | 8.605 ± 0.084 | 100 | | | |
| 12.6 ± 0.1 | 7.048 ± 0.056 | 29 | | | |
| 12.9 ± 0.1 | 6.842 ± 0.053 | 23 | | | |
| 17.8 ± 0.1 | 4.994 ± 0.028 | 43 | | | |
| 18.1 ± 0.1 | 4.896 ± 0.027 | 21 | | | |
| 20.7 ± 0.1 | 4.287 ± 0.021 | 22 | | | |
| 21.9 ± 0.1 | 4.062 ± 0.018 | 26 | | | |
| 22.5 ± 0.1 | 3.959 ± 0.017 | 38 | | | |
| 23.0 ± 0.1 | 3.874 ± 0.017 | 16 | | | |
| 23.3 ± 0.1 | 3.815 ± 0.016 | 20 | | | |
| 23.6 ± 0.1 | 3.764 ± 0.016 | 21 | | | |
| 24.3 ± 0.1 | 3.663 ± 0.015 | 31 | | | |
| 25.2 ± 0.1 | 3.531 ± 0.014 | 66 | | | |
| 26.0 ± 0.1 | 3.425 ± 0.013 | 23 | | | |
| 27.3 ± 0.1 | 3.267 ± 0.012 | 14 | | | |
| 27.9 ± 0.1 | 3.198 ± 0.011 | 11 | | | |
| 28.5 ± 0.1 | 3.132 ± 0.011 | 32 | | | |

-continued

| Pattern D Observed | | | Pattern D Representative | | |
|---|---|---|---|---|---|
| °2θ | d space (Å) | Intensity (%) | °2θ | d space (Å) | Intensity (%) |
| 28.9 ± 0.1 | 3.087 ± 0.010 | 29 | | | |
| 29.7 ± 0.1 | 3.012 ± 0.010 | 18 | | | |

Example 6C

Preparation of Sodium 2-(5-bromo-4-(4-cyclopropyl-naphthalen-1-yl)-4H-1,2,4-triazol-3-ylthio)acetate Displaying Unique Crystalline X-Ray Powder Diffraction Pattern E Preparation i:
A portion of Form A was mixed with ethanol and water (1/1) to form a slurry, which then underwent slow evaporation/fast evaporation in a cold room.

Preparation ii:
A portion of Form A was mixed with isopropyl alcohol and water (9/1) to form a slurry, which was slow cooled from 50° C., and then underwent slow evaporation/fast evaporation in a refrigerator. One Bruker pattern was analyzed for this material, and preferred orientation and particle statistic effects assessed through evaluation of the two dimensional scattering pattern. Consistent, uninterrupted rings devoid of spots suggest good particle and orientation statistics. XRPD pattern E is shown in FIG. 11; observed and representative peaks in the XRPD pattern are shown in the table below:

| Pattern E Observed | | | Pattern E Representative | | |
|---|---|---|---|---|---|
| °2θ | d space (Å) | Intensity (%) | °2θ | d space (Å) | Intensity (%) |
| 6.8 ± 0.1 | 13.038 ± 0.195 | 38 | 10.5 ± 0.1 | 8.425 ± 0.081 | 100 |
| 7.6 ± 0.1 | 11.694 ± 0.157 | 17 | 22.9 ± 0.1 | 3.890 ± 0.017 | 64 |

-continued

| Pattern E Observed | | | Pattern E Representative | | |
|---|---|---|---|---|---|
| °2θ | d space (Å) | Intensity (%) | °2θ | d space (Å) | Intensity (%) |
| 8.5 ± 0.1 | 10.378 ± 0.123 | 20 | 23.2 ± 0.1 | 3.834 ± 0.016 | 70 |
| 10.0 ± 0.1 | 8.828 ± 0.089 | 21 | 24.6 ± 0.1 | 3.616 ± 0.015 | 60 |
| 10.5 ± 0.1 | 8.425 ± 0.081 | 100 | | | |
| 11.3 ± 0.1 | 7.844 ± 0.070 | 32 | | | |
| 12.2 ± 0.1 | 7.243 ± 0.060 | 38 | | | |
| 12.9 ± 0.1 | 6.863 ± 0.053 | 33 | | | |
| 13.3 ± 0.1 | 6.647 ± 0.050 | 15 | | | |
| 13.8 ± 0.1 | 6.417 ± 0.047 | 14 | | | |
| 14.7 ± 0.1 | 6.026 ± 0.041 | 7 | | | |
| 15.5 ± 0.1 | 5.724 ± 0.037 | 13 | | | |
| 15.8 ± 0.1 | 5.623 ± 0.036 | 15 | | | |
| 16.2 ± 0.1 | 5.471 ± 0.034 | 7 | | | |
| 16.6 ± 0.1 | 5.328 ± 0.032 | 11 | | | |
| 17.1 ± 0.1 | 5.198 ± 0.030 | 28 | | | |
| 17.5 ± 0.1 | 5.068 ± 0.029 | 45 | | | |
| 19.4 ± 0.1 | 4.566 ± 0.023 | 9 | | | |
| 20.2 ± 0.1 | 4.405 ± 0.022 | 16 | | | |
| 21.1 ± 0.1 | 4.215 ± 0.020 | 26 | | | |
| 21.8 ± 0.1 | 4.081 ± 0.019 | 32 | | | |
| 22.4 ± 0.1 | 3.973 ± 0.018 | 33 | | | |
| 22.9 ± 0.1 | 3.890 ± 0.017 | 64 | | | |
| 23.2 ± 0.1 | 3.834 ± 0.016 | 70 | | | |
| 23.8 ± 0.1 | 3.739 ± 0.016 | 49 | | | |
| 24.6 ± 0.1 | 3.616 ± 0.015 | 60 | | | |
| 25.7 ± 0.1 | 3.472 ± 0.013 | 34 | | | |
| 26.2 ± 0.1 | 3.396 ± 0.013 | 44 | | | |
| 27.2 ± 0.1 | 3.283 ± 0.012 | 26 | | | |
| 28.1 ± 0.1 | 3.176 ± 0.011 | 45 | | | |
| 28.7 ± 0.1 | 3.115 ± 0.011 | 35 | | | |
| 29.1 ± 0.1 | 3.071 ± 0.010 | 32 | | | |
| 29.5 ± 0.1 | 3.028 ± 0.010 | 43 | | | |
| 30.0 ± 0.1 | 2.979 ± 0.010 | 36 | | | |

Mesophase Patterns 1, 2 and 3

Example 7A

Sodium 2-(5-bromo-4-(4-cyclopropylnaphthalen-1-yl)-4H-1,2,4-triazol-3-ylthio)acetate Displaying Mesophase Pattern 1

Solids isolated via various procedures outlined below, produced a mesophase material, designated as mesophase 1 (mesophase indicates an X-ray amorphous pattern with relatively few reflections, suggesting limited order in the solids), which shows a strong broad reflection at ~4°2θ, but no birefringence by optical microscopy:

a) evaporation from methanol, ethanol, acetone, methyl ethyl ketone, methyl ethyl ketone+heptanes or water;
b) vacuum drying Form A;
c) vacuum drying a mixture of Form A and pattern C at ambient temperature for ~23 hours;
d) precipitation from an acetonitrile slurry;
e) precipitation from slurries of Form A and Form B' in 2-propanol, prepared at ambient and cold room temperatures (~2-8° C.).

Figure 12:
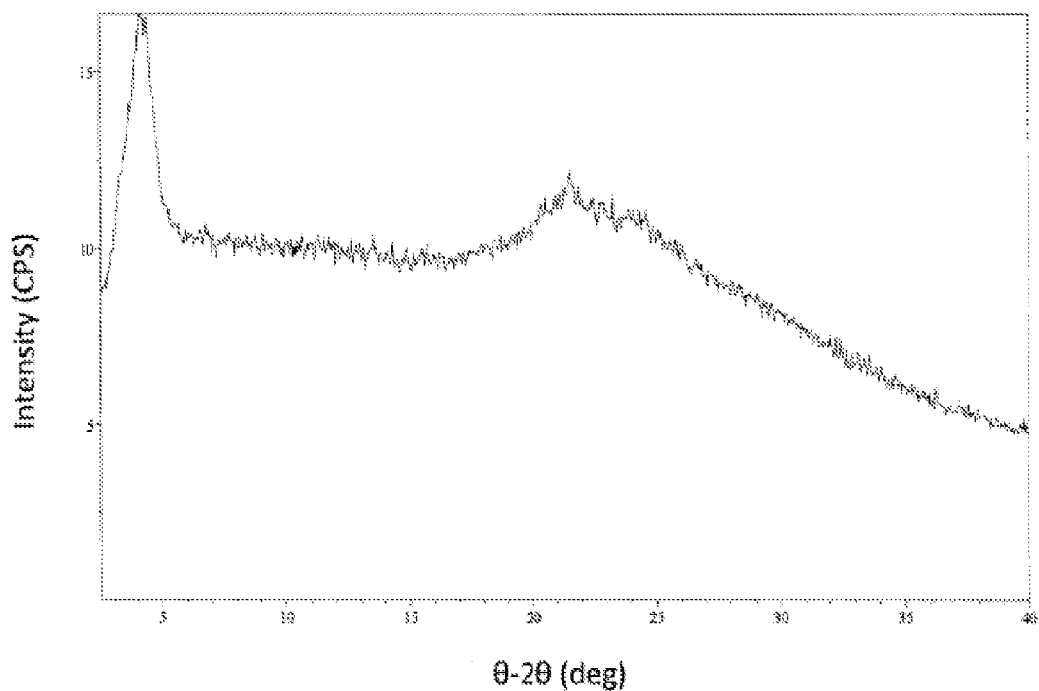
FIG. 12 represents an illustrative X-ray Powder Diffraction Pattern of Mesophase 1.

The x-ray powder diffraction pattern of Mesophase Pattern 1 is shown in FIG. 12.

Figure 13:
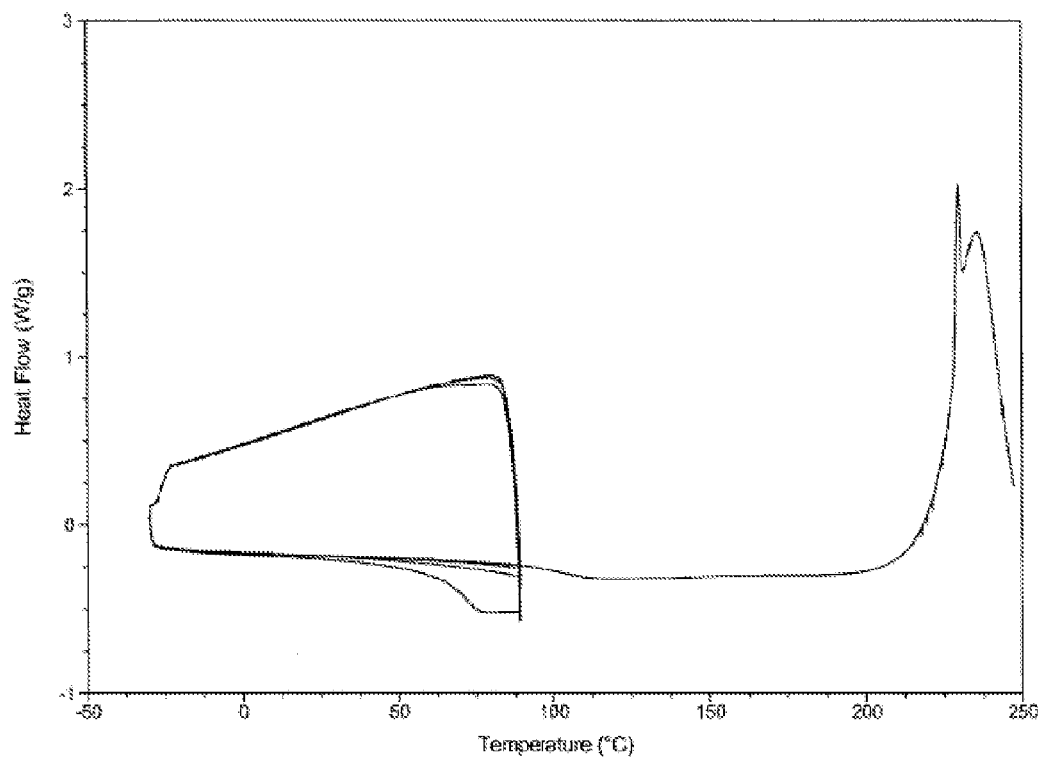
FIG. 13 represents an illustrative Cyclic Differential Scanning calorimetry Pattern of Mesophase 1.

The cyclic differential scanning calorimetry trace of Mesophase Pattern 1 is shown in FIG. 13.

Example 7B

Sodium 2-(5-bromo-4-(4-cyclopropylnaphthalen-1-yl)-4H-1,2,4-triazol-3-ylthio)acetate Displaying Mesophase Pattern 2

Mesophase pattern 2 solids were prepared by precipitation from 2-propanol/ethanol, and exhibits a strong sharp reflection at ~3°2θ and various potential weak broad reflections.

Figure 14:
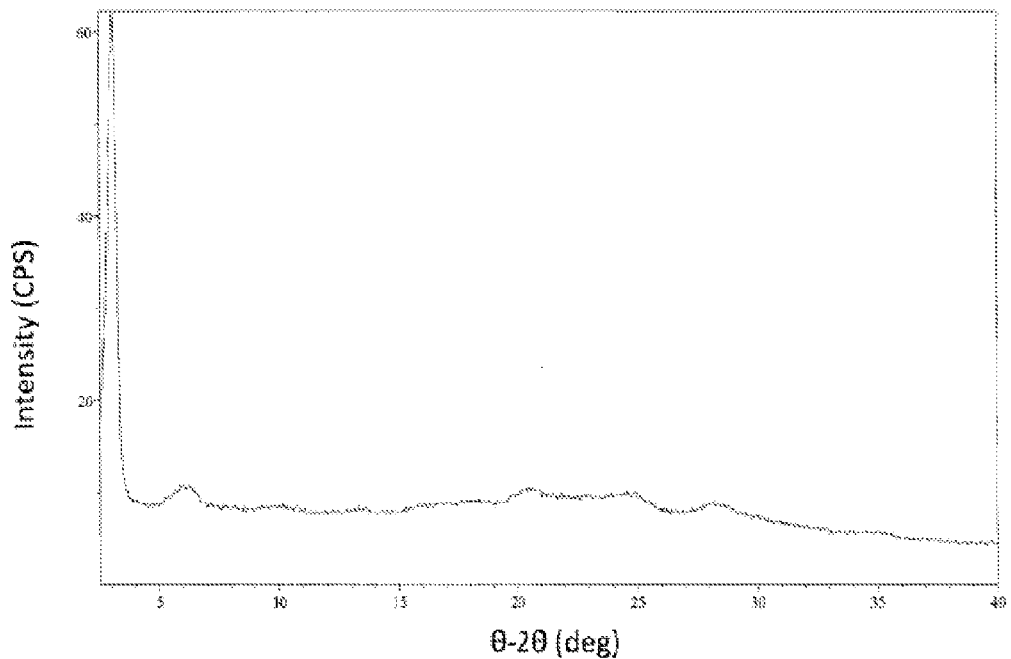
FIG. 14 represents an illustrative X-ray Powder Diffraction Pattern of Mesophase 2.

The x-ray powder diffraction pattern of Mesophase Pattern 2 is shown in FIG. 14.

Example 7C

Sodium 2-(5-bromo-4-(4-cyclopropylnaphthalen-1-yl)-4H-1,2,4-triazol-3-ylthio)acetate Displaying Mesophase Pattern 3

Mesophase pattern 3 solids were prepared by evaporation under vapor stress. Dichloromethane and tetrahydrofuran solutions were evaporated at ~97% relative humidity initially generating oils, which gradually exhibited partial crystallization and eventual stiffened to a gel.

Figure 15:
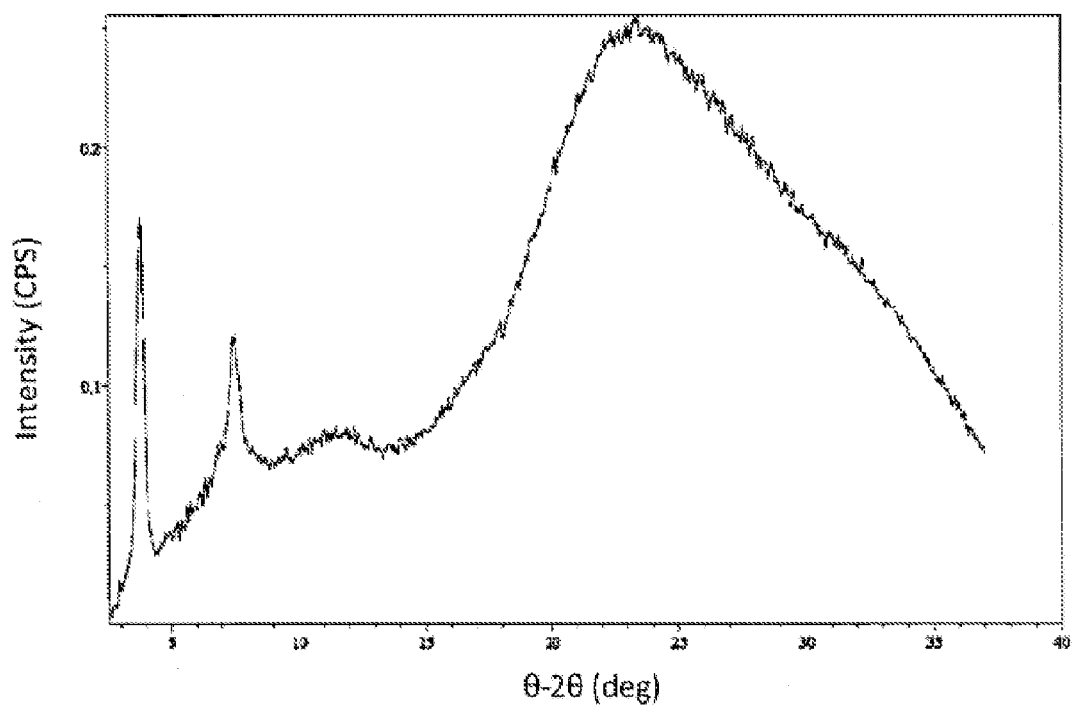
FIG. 15 represents an illustrative X-ray Powder Diffraction Pattern of Mesophase 3.

The x-ray powder diffraction pattern of Mesophase Pattern 3 is shown in FIG. 15. Note that crystalline solids signals may be obscured by the gel.

Example 8

Karl Fischer Water Content Determination

Coulometric Karl Fischer (KF) analysis for water determination was performed using a Mettler Toledo DL39 KF titrator. A blank titration was carried out prior to analysis. The sample was prepared under a dry nitrogen atmosphere; where ~1-13 mg of the sample were dissolved in approximately 1 mL dry Hydranal-Coulomat AD in a pre-dried vial. The entire solution was added to the Karl Fischer coulometer through a septum and mixed for 10 seconds. The sample was then titrated by means of a generator electrode, which produces iodine by electrochemical oxidation ($2\,I^- \rightarrow I_2 + 2e^-$). Samples were run in duplicate; the mean values are shown below, measured to the nearest tenth of a percent.

| Karl Fisher analysis (% wt water) | |
|---|---|
| Form A | 10.2% (Average of two lots) |
| Form B' | 2.3% |

III Instrument Techniques

Example 9

X-Ray Powder Diffraction (XRPD)

X-ray powder diffraction patterns were collected using an Inel XRG-3000 diffractometer equipped with a curved position sensitive detector with a 2θ range of 120°. An incident beam of Cu Kα radiation (40 kV, 30 mA) was used to collect data in real time at a resolution of 0.03°2θ. Prior to the analysis, a silicon standard (NIST SRM 640c) was analyzed to verify the Si 111 peak position. Samples were prepared for analysis by packing them into thin-walled glass capillaries.

Each capillary was mounted onto a goniometer head and rotated during data acquisition. The monochromator slit was set at 5 mm by 160 μm.

Alternatively, X-ray powder diffraction patterns were collected using a Bruker D-8 Discover diffractometer and Bruker's General Detector System (GADDS, v. 4.1.20). An incident microbeam of Cu Kα radiation was produced using a fine-focus tube (40 kV, 40 mA), a Göbel mirror, and a 0.5 mm double-pinhole collimator. Prior to the analysis, a silicon standard (NIST SRM 640c) was analyzed to verify the Si 111 peak position. The sample was packed between 3 μm thick films to form a portable, disc-shaped specimen. The prepared specimen was loaded in a holder secured to a translation stage. A video camera and laser were used to position the area of interest to intersect the incident beam in transmission geometry. The incident beam was scanned and rastered to optimize orientation statistics. A beam-stop was used to minimize air scatter from the incident beam. Diffraction patterns were collected using a Hi-Star area detector located 15 cm from the sample and processed using GADDS. The intensity in the GADDS image of the diffraction pattern was integrated using a step size of 0.04°2θ. The integrated patterns display diffraction intensity as a function of 2θ.

Or, X-ray powder diffraction patterns were collected using a Panalytical X'Pert Pro diffractometer. An incident beam of Cu Kα radiation was produced using an Optix long, fine-focus source. An elliptically graded multilayer mirror was used to focus the Cu Kα X-rays of the source through the specimen and onto the detector. Data were collected and analyzed using X'Pert Pro Data Collector software (v. 2.2b). Prior to the analysis, a silicon specimen (NIST SRM 640c) was analyzed to verify the Si 111 peak position. The specimen was sandwiched between 3 μm thick films, analyzed in transmission geometry, and rotated to optimize orientation statistics. A beam-stop was used to minimize the background generated by air scattering. Soller slits were used for the incident and diffracted beams to minimize axial divergence. Diffraction patterns were collected using a scanning position-sensitive detector (X'Celerator) located 240 mm from the specimen.

Peaks within the range of up to about 30°2θ are listed in the tables, although different rounding algorithms were used to round each peak to the nearest 0.1° or 0.01°2θ, depending upon the instrument used to collect the data and/or the inherent peak resolution. The location of the peaks along the x-axis (°2θ) in the tables were automatically determined using PatternMatch™ 3.0.1 and rounded to one or two significant figures after the decimal point based upon the above criteria. Peak position variabilities are given to within ±0.1°2θ based upon recommendations outlined in United States Pharmacopeia, USP 32, NF 27, Vol. 1, pg. 392, 2009. The wavelength used to calculate d-spacings was 1.541874 Å, a weighted average of the Cu—$K_{\alpha 1}$ and Cu—$K_{\alpha 2}$ wavelengths. Variability associated with d-spacing estimates was calculated from the USP recommendation, at each d-spacing.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as Representative Peaks.

Characteristic peaks are a subset of Representative Peaks and are used to differentiate one crystalline polymorph from another crystalline polymorph. Characteristic peaks are determined by evaluating which representative peaks, if any, are present in one crystalline polymorph of a compound against all other known crystalline polymorphs of that compound to within ±0.1°2θ. Not all crystalline polymorphs of a compound necessarily have at least one characteristic peak.

Example 10

Differential Scanning Calorimetry (DSC)

Differential scanning calorimetry was performed using a TA Instruments Q2000 differential scanning calorimeter. Temperature calibration was performed using NIST traceable indium metal. The sample was placed into an aluminum DSC pan, and the weight was accurately recorded. The pan was covered with a lid, and the lid was crimped. A weighed, crimped aluminum pan was placed on the reference side of the cell. The sample cell was equilibrated at the initial temperature and heated under a nitrogen purge. To measure glass transition temperature ($T_g$) the sample cell was first equilibrated at −30° C., and then heated under nitrogen gas at a rate of 10° C./min, cycling three times to 90° C. Each cycle, the sample cell was allowed to cool and equilibrate at −30° C. The sample cell was then heated at 10° C./min to a final temperature of 250° C.

Example 11

Infrared Spectroscopy (IR)

IR spectra were acquired on a Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. Wavelength verification was performed using NIST SRM 1921b (polystyrene). A diffuse reflectance accessory (the Collector™, Thermo Spectra-Tech) was used for sampling. Sample preparation consisted of physically mixing the sample with KBr, placing the sample into a 13 mm diameter cup and leveling the material. The background data set was acquired with KBr powder. A Log 1/R(R=reflectance) spectrum was obtained by taking a ratio of these two data sets against each other and then converting to Kubelka-Munk units.

Example 12

FT-Raman Spectroscopy

Raman spectra were acquired on a FT-Raman 960 spectrometer (Thermo Nicolet) equipped with an indium gallium arsenide (InGaAs) detector. Wavelength verification was performed using sulfur and cyclohexane. Each sample was prepared for analysis by placing the sample into a glass tube and positioning the tube in a gold-coated tube holder. The sample was irradiated with a Nd:YVO$_4$ laser (1064 nm excitation wavelength).

What is claimed is:

1. A crystalline polymorph of sodium 2-(5-bromo-4-(4-cyclopropylnaphthalen-1-yl)-4H-1,2,4-triazol-3-ylthio)acetate:

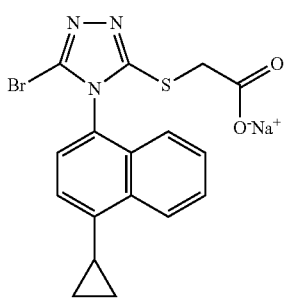

characterized by peaks at 4.90, 9.83, and 25.29°2θ±0.1°2θ.

2. The crystalline polymorph of claim 1, further characterized by at least two further peaks at 6.86, 8.41, 10.13, 17.92, and 23.10°2θ±0.1°2θ.

3. The crystalline polymorph of claim 1 that exhibits an x-ray powder diffraction pattern substantially the same as the x-ray powder diffraction pattern shown in FIG. 1.

4. A crystalline polymorph of sodium 2-(5-bromo-4-(4-cyclopropylnaphthalen-1-yl)-4H-1,2,4-triazol-3-ylthio)acetate of claim 1:

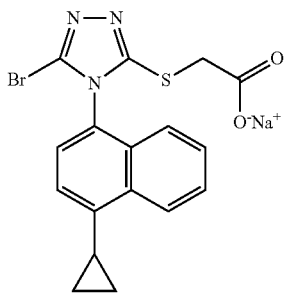

characterized by an endothermic point onset, as determined by differential scanning calorimetry at about 62° C.

5. The crystalline polymorph of claim 4 characterized by a differential scanning calorimetry pattern substantially the same as the differential scanning calorimetry pattern shown in FIG. 2.

6. A solid pharmaceutical composition comprising an effective amount of the crystalline polymorph of claim 1 as an active ingredient and at least one excipient or carrier.

7. A solid pharmaceutical composition comprising an effective amount of the crystalline polymorph of claim 4 as an active ingredient and at least one excipient or carrier.

8. A method for treating hyperuricemia, or a disease caused by elevated uric acid levels, comprising administering an effective amount of the crystalline polymorph of claim 1.

9. A method for treating hyperuricemia, or a disease caused by elevated uric acid levels, comprising administering an effective amount of the crystalline polymorph of claim 4.

10. A method for treating gout, comprising administering an effective amount of the crystalline polymorph of claim 1.

11. A method for treating gout, comprising administering an effective amount of the crystalline polymorph of claim 4.

12. A solid pharmaceutical composition comprising an effective amount of at least two of the forms of sodium 2-(5-bromo-4-(4-cyclopropylnaphthalen-1-yl)-4H-1,2,4-triazol-3-ylthio)acetate selected from the group consisting of
crystalline polymorph Form A as an active ingredient characterized by peaks at 4.90, 9.83, and 25.29°2θ±0.1°2θ;
crystalline polymorph Form B as an active ingredient characterized by peaks at 4.22, 8.51, and 16.95°2θ±0.1°2θ;
crystalline polymorph Form B' as an active ingredient that exhibits an x-ray powder diffraction pattern substantially the same as the x-ray powder diffraction pattern shown in FIG. 7;
crystalline Form C as an active ingredient characterized by peaks at 6.9, 10.1 and 22.6°2θ±0.1°2θ;
crystalline Form D as an active ingredient characterized by peaks at 10.3, 17.8 and 25.2°2θ±0.1°2θ;
crystalline Form E as an active ingredient characterized by at least three peaks 10.5, 22.9, 23.2 or 24.6°2θ±0.1°2θ;
and at least one excipient or carrier.

13. A method for treating hyperuricemia or a disease caused by elevated uric acid levels, comprising administering an effective amount of at least two of the forms of sodium 2-(5-bromo-4-(4-cyclopropylnaphthalen-1-yl)-4H-1,2,4-triazol-3-ylthio)acetate selected from the group consisting of:
crystalline polymorph Form A as an active ingredient characterized by peaks at 4.90, 9.83 and 25.29°2θ±0.1°2θ;
crystalline polymorph Form B as an active ingredient characterized by peaks at 4.22, 8.51, and 16.95°2θ±0.1°2θ;
crystalline polymorph Form B' as an active ingredient that exhibits an x-ray powder diffraction pattern substantially the same as the x-ray powder diffraction pattern shown in FIG. 7;
crystalline Form C as an active ingredient characterized by peaks at 6.9, 10.1 and 22.6°2θ±0.1°2θ;
crystalline Form D as an active ingredient characterized by peaks at 10.3, 17.8 and 25.2°2θ±0.1°2θ;
crystalline Form E as an active ingredient characterized by at least three peaks 10.5, 22.9, 23.2 or 24.6°2θ±0.1°2θ;
and at least one excipient or carrier.

14. A method for treating gout, comprising administering an effective amount of at least two of the forms of sodium 2-(5-bromo-4-(4-cyclopropylnaphthalen-1-yl)-4H-1,2,4-triazol-3-ylthio)acetate selected from the group consisting of:
crystalline polymorph Form A as an active ingredient characterized by peaks at 4.90, 9.83, and 25.29°2θ±0.1°2θ;
crystalline polymorph Form B as an active ingredient characterized by peaks at 4.22, 8.51, and 16.95°2θ±0.1°2θ;
crystalline polymorph Form B' as an active ingredient that exhibits an x-ray powder diffraction pattern substantially the same as the x-ray powder diffraction pattern shown in FIG. 7;
crystalline Form C as an active ingredient characterized by peaks at 6.9, 10.1 and 22.6°2θ±0.1°2θ;
crystalline Form D as an active ingredient characterized by peaks at 10.3, 17.8 and 25.2°2θ±0.1°2θ;
crystalline Form E as an active ingredient characterized by at least three peaks 10.5, 22.9, 23.2 or 24.6°2θ±0.1°2θ;
and at least one excipient or carrier.

15. A method for preparing a crystalline polymorph of sodium 2-(5-bromo-4-(4-cyclopropylnaphthalen-1-yl)-4H-1,2,4-triazol-3-ylthio)acetate, comprising:
a) contacting amorphous sodium 2-(5-bromo-4-(4-cyclopropylnaphthalen-1-yl)-4H-1,2,4-triazol-3-ylthio)acetate with water and an aprotic solvent; and
b) isolating the solids from the mixture prepared in step a).

16. The method of claim 15, wherein the aprotic solvent is ethyl acetate.

17. The method of claim 15, wherein step b) further comprises drying the isolated solids.

18. The method of claim 15, wherein step b) further comprises drying the isolated solids under vacuum.

19. The method of claim 15, wherein the crystalline polymorph prepared is Form A.

20. The method of claim 15, wherein the contacting step a) is for about 18 hours.

* * * * *

UNITED STATES PATENT AND TRADEMARK OFFICE
CERTIFICATE OF CORRECTION

PATENT NO.         : 8,524,754 B2
APPLICATION NO.    : 13/375607
DATED              : September 3, 2013
INVENTOR(S)        : Zamansky et al.

It is certified that error appears in the above-identified patent and that said Letters Patent is hereby corrected as shown below:

In the Claims

Column 44, lines 50-52, Claim 15, delete:

"A method for preparing a crystalline polymorph of sodium 2-(5-bromo-4-(4-cyclopropylnaphthalen-1-yl)-4H-1,2,4-triazol-3-ylthio )acetate, comprising:"

and replace with:

--A method for preparing a crystalline polymorph of sodium 2-(5-bromo-4-(4-cyclopropylnaphthalen-1-yl)-4H-1,2,4-triazol-3-ylthio )acetate of claim 1, comprising:--

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,524,754 B2                                                                 Page 1 of 1
APPLICATION NO.  : 13/375607
DATED            : September 3, 2013
INVENTOR(S)      : Zamansky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Twenty-third Day of May, 2017

Michelle K. Lee
*Director of the United States Patent and Trademark Office*